US012048414B2

(12) United States Patent
Sasada et al.

(10) Patent No.: US 12,048,414 B2
(45) Date of Patent: Jul. 30, 2024

(54) MEDICAL SUPPORT SYSTEM, MEDICAL SUPPORT DEVICE, AND MEDICAL SUPPORT METHOD

(71) Applicant: Sony Group Corporation, Tokyo (JP)

(72) Inventors: Shiori Sasada, Kanagawa (JP); Kento Takenaka, Tokyo (JP); Kazuo Ohtsuka, Tokyo (JP); Mamoru Watanabe, Tokyo (JP)

(73) Assignee: Sony Group Corporation, Tokyo (JP)

( * ) Notice: Subject to any disclaimer, the term of this patent is extended or adjusted under 35 U.S.C. 154(b) by 359 days.

(21) Appl. No.: 17/311,284

(22) PCT Filed: Dec. 4, 2019

(86) PCT No.: PCT/JP2019/047351
§ 371 (c)(1),
(2) Date: Jun. 4, 2021

(87) PCT Pub. No.: WO2020/121906
PCT Pub. Date: Jun. 18, 2020

(65) Prior Publication Data
US 2022/0020147 A1 Jan. 20, 2022

(30) Foreign Application Priority Data

Dec. 13, 2018 (JP) ................................. 2018-233204
Feb. 12, 2019 (JP) ................................. 2019-022255

(51) Int. Cl.
*G06T 7/11* (2017.01)
*A61B 1/00* (2006.01)
(Continued)

(52) U.S. Cl.
CPC .. *A61B 1/000094* (2022.02); *A61B 1/000096* (2022.02); *A61B 1/0005* (2013.01);
(Continued)

(58) Field of Classification Search
CPC ........ A61B 1/000094; A61B 1/000096; A61B 1/0005; A61B 1/00055; G06T 3/40;
(Continued)

(56) References Cited

U.S. PATENT DOCUMENTS

2009/0019381 A1* 1/2009 Kimoto .............. A61B 1/00042
715/764
2016/0070949 A1 3/2016 Tunstall et al.
(Continued)

FOREIGN PATENT DOCUMENTS

CN 101273916 A 10/2008
WO WO 2016/151711 A1 9/2016
(Continued)

OTHER PUBLICATIONS

International Preliminary Report on Patentability and English translation thereof dated Jun. 24, 2021 in connection with International Application No. PCT/JP2019/047351.
(Continued)

*Primary Examiner* — Charlotte M Baker
(74) *Attorney, Agent, or Firm* — Wolf, Greenfield & Sacks, P.C.

(57) ABSTRACT

There is provided a medical support system including: a derivation device that derives an assessment value for an affected site based on an affected site image obtained by imaging the affected site; and a display device that presents the assessment value to a user, in which the derivation device includes: a cut-out unit that cuts out the affected site image as a plurality of tile images having tile shapes; and an assessment derivation unit that derives a tile assessment value representing an assessment of the affected site in the plurality of the tile images by using a determiner obtained by machine learning.

19 Claims, 10 Drawing Sheets

(51) Int. Cl.
  *G06T 3/40*    (2006.01)
  *G06T 7/00*    (2017.01)
  *G06T 11/00*   (2006.01)
  *G16H 30/40*   (2018.01)
  *G16H 50/20*   (2018.01)
  *G16H 50/30*   (2018.01)
  *H04N 7/18*    (2006.01)
  *H04N 23/50*   (2023.01)

(52) U.S. Cl.
  CPC .............. *G06T 3/40* (2013.01); *G06T 7/0012* (2013.01); *G06T 7/11* (2017.01); *G06T 11/00* (2013.01); *G16H 30/40* (2018.01); *G16H 50/20* (2018.01); *G16H 50/30* (2018.01); *H04N 7/183* (2013.01); *G06T 2207/10068* (2013.01); *G06T 2207/20021* (2013.01); *G06T 2207/30004* (2013.01); *H04N 23/555* (2023.01)

(58) Field of Classification Search
  CPC ......... G06T 7/0012; G06T 7/11; G06T 11/00; G06T 2207/10068; G06T 2207/20021; G06T 2207/30004; G06T 2207/30028; G16H 30/40; G16H 50/20; G16H 50/30; H04N 7/183; H04N 23/555
  USPC ....................................................... 382/128
  See application file for complete search history.

(56) References Cited

U.S. PATENT DOCUMENTS

| | | |
|---|---|---|
| 2017/0161891 A1 | 6/2017 | Madabhushi et al. |
| 2018/0014902 A1 | 1/2018 | Kitamura et al. |
| 2018/0146844 A1 | 5/2018 | Okazaki |
| 2018/0184882 A1 | 7/2018 | Makino |
| 2018/0256145 A1 | 9/2018 | Tesar |
| 2018/0322631 A1 | 11/2018 | Madabhushi et al. |
| 2020/0022560 A1 | 1/2020 | Oosake |
| 2021/0407309 A1* | 12/2021 | Jarc ............ G16H 40/63 |

FOREIGN PATENT DOCUMENTS

| | | |
|---|---|---|
| WO | WO-2018065482 A1 | 4/2018 |
| WO | WO 2018/180631 A1 | 10/2018 |

OTHER PUBLICATIONS

Extended European Search Report dated Dec. 13, 2021 in connection with European Application No. 19894778.0.

International Search Report and English translation thereof dated Feb. 4, 2020 in connection with International Application No. PCT/JP2019/047351.

International Written Opinion and English translation thereof mailed Feb. 4, 2020 in connection with International Application No. PCT/JP2019/047351.

Levin et al., Complications of colonoscopy in an integrated health care delivery system. Annals of internal medicine. Dec. 1, 20069;145(12):880-6.

* cited by examiner

MEDICAL SUPPORT SYSTEM, MEDICAL SUPPORT DEVICE, AND MEDICAL SUPPORT METHOD

CROSS-REFERENCE TO RELATED APPLICATIONS

This application claims the benefit under 35 U.S.C. § 371 as a U.S. National Stage Entry of International Application No. PCT/JP2019/047351, filed in the Japanese Patent Office as a Receiving Office on Dec. 4, 2019, which claims priority to Japanese Patent Application Number JP2019-022255, filed in the Japanese Patent Office on Feb. 12, 2019 and Japanese Patent Application Number JP2018-233204, filed in the Japanese Patent Office on Dec. 13, 2018, each of which is hereby incorporated by reference in its entirety.

FIELD

The present disclosure relates to a medical support system, a medical support device, and a medical support method.

BACKGROUND

Various techniques are used by physicians in execution of medical practice on patients. For example, in the case of ulcerative colitis or the like, medical practice is performed using an endoscope. In this medical practice, a physician assesses pathological conditions of an affected site from an image obtained through an endoscope and controls the dosage or the like while continuing monitoring for a long period of time. In cases where it is difficult to assess the pathological condition by follow-up by such monitoring, a biopsy might be performed to make a definitive diagnosis by pathological diagnosis (refer to Non Patent Literature below).

CITATION LIST

Non Patent Literature

Non Patent Literature 1: Theodore R. Levin, "Complications of Colonoscopy in an Integrated Health Care Delivery System", Ann Intern Med, 2006 Dec. 19, 145 (12): 880-6.

SUMMARY

Technical Problem

However, the assessment of the pathological condition based on the endoscopic image is a visual judgment, leading to occurrence of assessment variation depending on individual specialists. In addition, when a biopsy is performed for a medical examination, as described in Non Patent Literature 1 above, there is a concern of risk to the living body such as bleeding due to the influence of perforation during sample collection, leading to affection of infectious disease. In view of the above circumstances, there has been a demand for capability of facilitating assessment of pathological conditions in the endoscopic examination.

Solution to Problem

According to the present disclosure, a medical support system comprising: a derivation device that derives an assessment value for an affected site based on an affected site image obtained by imaging the affected site; and a display device that presents the assessment value to a user, wherein the derivation device includes: a cut-out unit that cuts out the affected site image as a plurality of tile images having tile shapes; and an assessment derivation unit that derives a tile assessment value representing an assessment of the affected site in the plurality of the tile images by using a determiner obtained by machine learning is provided.

Furthermore, according to the present disclosure, a medical support device comprising: a cut-out unit that cuts out an affected site image obtained by imaging an affected site as a plurality of tile images having tile shapes; an assessment derivation unit that derives a tile assessment value representing an assessment of the affected site in the plurality of the tile images by using a determiner obtained by machine learning; and a display control unit that controls a display device that presents the tile assessment value to a user is provided.

Moreover, according to the present disclosure, a medical support method comprising: cutting out, by a derivation device, an affected site image obtained by imaging an affected site as a plurality of tile images having tile shapes, and deriving, by the derivation device, a tile assessment value representing an assessment of the affected site in the plurality of the tile images by using a determiner obtained by machine learning; and presenting, by a display device, the tile assessment value to a user is provided.

DESCRIPTION OF EMBODIMENTS

A preferred embodiment of the present disclosure will be described in detail hereinbelow with reference to the accompanying drawings. Note that redundant descriptions will be omitted from the present specification and the drawings by assigning the same reference signs to components having substantially the same functional configuration.

Note that the description will be provided in the following order.
1. Technical overview
2. Embodiments
2.1. Functions and configuration
2.2. Operation flow
3. Modification
4. Examples
5. Hardware configuration example

1. Technical Overview

Figure 1:
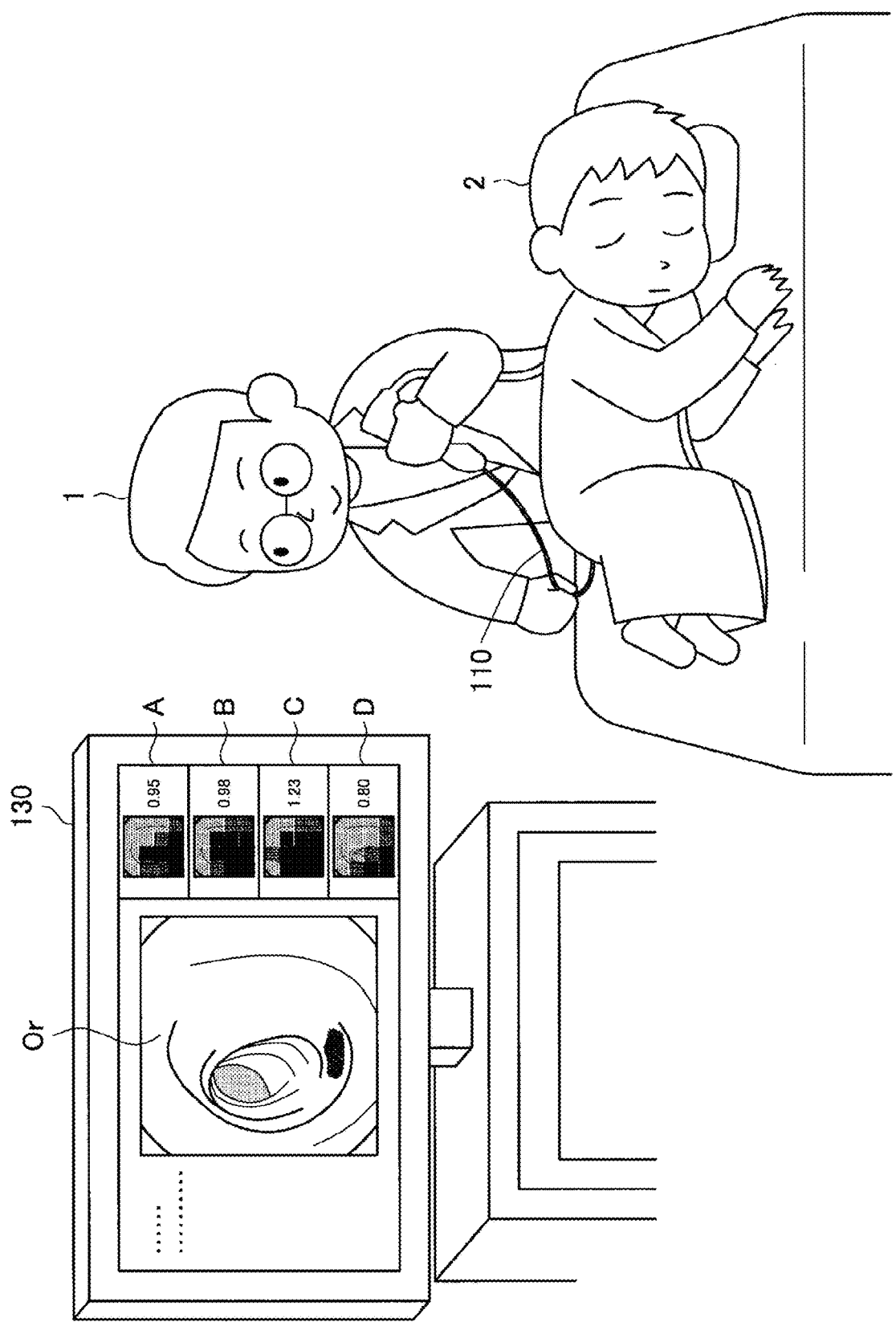
FIG. 1 is a schematic diagram illustrating an overview of a medical support system according to an embodiment of the present disclosure.
Figure 2:
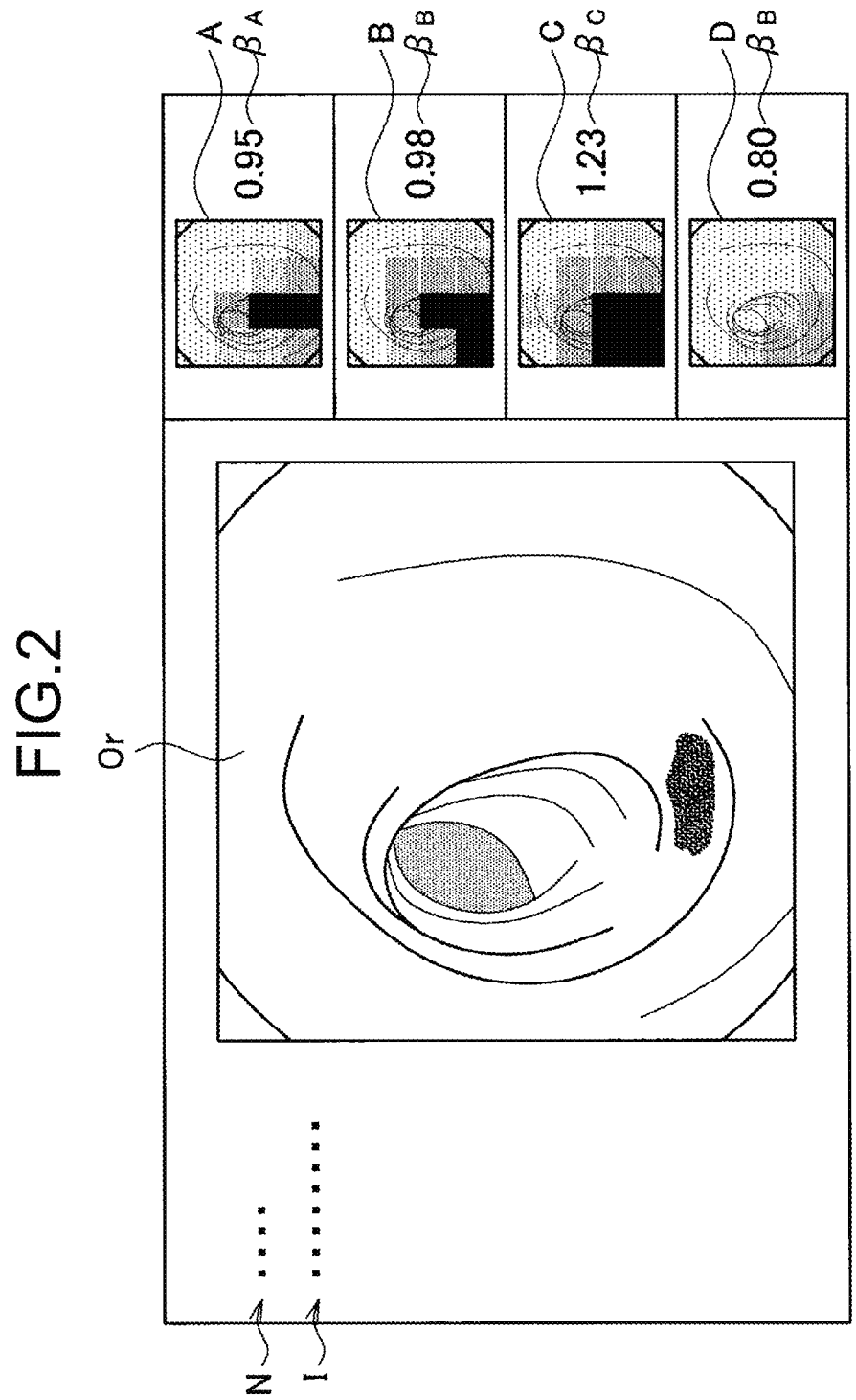
FIG. 2 is a diagram illustrating an example of a display according to the same embodiment.

First, a technical overview of a medical support system according to an embodiment of the present disclosure will be described with reference to FIGS. 1 and 2. FIG. 1 is a diagram illustrating a technical overview regarding the technology according to the present disclosure. FIG. 2 is a diagram illustrating an example of an affected site image displayed on a display device included in the medical support system.

Referring to FIGS. 1 and 2, in the examination of gastrointestinal diseases, a physician 1 examines the inside of the patient 2 using an endoscope 110, for example, and an affected site image Or of the inside of the patient's body imaged by the endoscope 110 is displayed on a display device 130. The physician 1 can examine the inside of the patient by visually inspecting the affected site image Or displayed on the display device 130. In the technique according to the present disclosure, the display device 130 displays, together with the affected site image Or, assessment images A to D of the pathological conditions of the affected site obtained by using machine learning are also superimposed and displayed over the affected site image Or. The physician 1 can improve the diagnosis accuracy by making a diagnosis in consideration of the assessment result of the pathological condition by machine learning.

Next, the assessment images A to D displayed on the display device 130 will be described with reference to FIG. 2. As illustrated in FIG. 2, the display device 130 displays, for example, patient's name N and detailed information I regarding the imaging of the endoscope 110, and further displays the affected site image Or captured by the endoscope as well as the assessment image A, the assessment image B, the assessment image C, and the assessment image D each presenting assessment of the affected site derived by using machine learning on the affected site image Or.

In a medical support system 1000, in addition to the assessment of the affected site presented by the assessment images A to D, overall assessment values $\beta_A$ to $\beta_D$ for each of the entire assessment images A to D can be further presented. In the assessment images A to D, the assessment of the affected site is presented in different colors or the like according to the assessment value of each of tiles which are cut out in tile shapes.

By using the medical support system 1000 as described above, the physician 1 can make a diagnosis of the pathological condition with higher confidence in consideration of the assessment of the affected site derived by the medical support system 1000 and own diagnosis.

The medical support system 1000 according to the present embodiment can be applied to an examination of a gastrointestinal disease using an endoscope, for example. Specifically, the medical support system 1000 can be suitably used for the examination of an inflammatory bowel disease such as ulcerative colitis or Crohn's disease. Although the present specification will describe an exemplary case where the medical support system 1000 according to the present embodiment is used for the examination of ulcerative colitis, it goes without saying that the technique according to the present disclosure is not limited to such an example.

2. Embodiments

The above medical support system 1000 will be described in detail below. The description of the medical support system 1000 will be an example of using an affected site image captured by an endoscope. The medical support system 1000 described below includes an endoscope 110, a derivation device 120, and a display device 130, but the endoscope 110 does not have to be included in the medical support system 1000. Furthermore, the display device 130 does not have to be included in the medical support system 1000.

2.1. Functions and Configurations

The medical support system 1000 includes the endoscope 110, the derivation device 120, and the display device 130. The medical support system 1000 has a function of operating the determiner generated by machine learning in the derivation device 120 by using the affected site image captured by the endoscope 110 as an input so as to derive an assessment value of the affected site and presenting on the display device 130 the assessment value of the affected site to the user.

The endoscope 110 has a function of imaging the inside of a patient and acquiring an affected site image. The affected site image is an image including an affected site examined by the physician. Specifically, the affected site image is an image in which the blood vessel image, irregularities, and ulcer part of the affected site have high visibility. The affected site image may be an image of the affected site captured by the endoscope, may be a moving image continuously captured by the endoscope, or may be a still image obtained by pausing the moving image captured by the endoscope. In a case where the affected site image is a moving image, the medical support system 1000 can present a tile assessment value described below to the user in real time, for example. Although the present embodiment illustrates an example in which an endoscope is used as an imaging device, the present embodiment is not limited to such an example. The imaging device that images the affected site is not limited in forms, and may be a known imaging device.

Specifically, as the captured image obtained by capturing the affected site, a white light image of an endoscope may be used. The white light image is an image that can be most easily captured by the basic functions of the endoscope. Therefore, when the pathological conditions can be assessed by a white light image, it is possible to suppress the time, items, and cost of endoscopy.

In the case of having difficulty assessing the pathological conditions with a white light image, for example, it is allowable to use an image obtained by Narrow Band Imaging (NBI) in which blood vessels are emphasized by special light, or a stained image obtained by applying indigo carmine staining that emphasizes irregularities. By additionally using these NBI images and stained images together with the white light image for the generation of the determiner included in the derivation device 120, it is possible to improve the assessment accuracy of the affected site.

The derivation device 120 has a cut-out unit 122 and an assessment derivation unit 124. The derivation device 120 has a function of deriving an assessment of pathological conditions of the affected site based on the affected site image. For example, the derivation device 120 may derive the assessment of the pathological conditions of the affected site by subdividing the affected site image, deriving an assessment value for the subdivided image, and further calculating an overall assessment value for the entire image based on each of the assessment values.

The cut-out unit 122 has a function of cutting out the affected site image captured by the endoscope 110 as a tile image, which has a polygonal tile shape. The cut-out unit 122 cuts out an affected site image as a plurality of tile images with a size capable of determining the pathological conditions of the affected site. The size capable of determining the pathological conditions of the affected site may be a size that can include an examination target such as a blood vessel image or an ulcer.

Specifically, the cut-out unit 122 may cut out an affected site image into a quadrangular shape such as a square. The cut-out unit 122 may cut out the affected site image so that the circumscribed circle of the quadrangular shape is 5 mm or more and 15 mm or less. The tile image cut out into a polygon includes at least the above-described examination target. The shape of the tile image is not limited to a polygon, and may be any shape capable of obtaining subdivided images of the affected site image. Furthermore, the tile image may be cut out into a random shape having a different shape depending on the location.

The assessment derivation unit 124 has a function of deriving a tile assessment value using a determiner obtained by machine learning based on the tile image cut out by the cut-out unit 122. The tile assessment value is an assessment value of the affected site derived for each of the tile images. The assessment value is either an assessment value for the pathological conditions of the affected site judged by a physician (endoscopist) by visual inspection of the surface of the affected site, or a pathological examination assessment value obtained by the diagnosis of a physician (pathologist) by pathologically examining the affected site.

Specifically, the assessment value for the pathological conditions of the affected site is an assessment value scored by the physician for bleeding, tumor, or visible vascular pattern in the affected site. The assessment value for the pathological condition of the affected site may be an assessment value obtained by any known scoring method.

For example, UCEIS score can be used as an assessment value for the pathological conditions of the affected site. The UCEIS score is an index that has recently come to be used as an assessment value indicating the severity of ulcerative colitis. The UCEIS score can perform precise classification, making it possible to formulate precise diagnostic policies and to reduce the assessment variation among endoscopists.

Specifically, the UCEIS score is defined for the assessment of at least vascular pattern, bleeding, and the erosions and ulcers in ulcerative colitis, as illustrated in Table 1 below. The assessment derivation unit 124 may derive assessment values for each of the vascular pattern, bleeding, and erosions and ulcers in ulcerative colitis.

TABLE 1

| Descriptor (Assessment Item) | Scale and Anchor points | Definition |
| --- | --- | --- |
| Vascular pattern | Normal (0) | Normal vascular pattern (with arborization of capillaries clearly defined, or with blurring or patchy loss of capillary margins). |

TABLE 1-continued

| Descriptor (Assessment Item) | Scale and Anchor points | Definition |
| --- | --- | --- |
| | Patchy obliteration (1) | Patchy obliteration of vascular pattern. |
| | Obliterated (2) | Complete obliteration of vascular pattern. |
| Bleeding | None (0) | No visible blood. |
| | Mucosal (1) | Some spots or streaks of coagulated blood on the surface of the mucosa, which can be washed away. |
| | Luminal mild (2) | Some free liquid blood in the lumen |
| | Luminal moderate or severe (3) | Frank blood in the lumen or visible oozing from mucosa or visible oozing from a hemorrhagic mucosa. |
| Erosions and ulcers | None (0) | Normal mucosa, no visible erosions or ulcers. |
| | Erosions (1) | Tiny (5 mm or less) defects in the mucosa, of a white or yellow color with a flat edge. |
| | Superficial ulcer (2) | Larger (5 mm or more) defects in the mucosa, which are discrete fibrin-covered ulcers. |
| | Deep ulcer (3) | Deeper excavated defects in the mucosa, with a slightly raised edge. |

In addition, the Mayo score can be used as an assessment value for the pathological condition of the affected site. The Mayo score can classify the severity of ulcerative colitis into several levels from 0 to 3. Specifically, the Mayo score has assessment values defined for a plurality of items as illustrated in Tables 2 to 5 below. The assessment derivation unit 124 may derive assessment values for each of vascular pattern, bleeding, and erosions and ulcers in ulcerative colitis, for each of endoscopic features, rectal bleeding, and physician's global assessment.

TABLE 2

| Score | Endoscopic features |
| --- | --- |
| 0 | Normal or inactive. |
| 1 | Mild (Erythema, decreased vascular pattern, mild friability). |
| 2 | Moderate (Marked erythema, absent vascular pattern, friability, erosions). |
| 3 | Severe (spontaneous bleeding, ulceration). |

TABLE 3

| Score | Rectal bleeding |
| --- | --- |
| 0 | No blood seen. |
| 1 | Streaks of blood with stool less than half the time. |
| 2 | Obvious blood with stool most of time. |
| 3 | Blood alone passes. |

TABLE 4

| Score | Stool frequency |
|---|---|
| 0 | Same degree as normal number of stools per day. |
| 1 | 1 to 2 stools more than normal per day. |
| 2 | 3 to 4 stools more than normal per day. |
| 3 | 5 or more stools more than normal per day. |

TABLE 5

| Score | Physician's global assessment |
|---|---|
| 0 | Normal. |
| 1 | Mild disease. |
| 2 | Moderate disease. |
| 3 | Severe disease. |

In the Mayo score, a case where the total score of the above individual items is 2 or less and none of the subscores exceeds 1 is defined as "Mayo score remission". In addition, in the Mayo score, the case where the Mayo score has decreased by 3 or more or 30% or more from the baseline, and the rectal bleeding subscore has decreased by 1 or more, or the rectal bleeding subscore is 0 or 1, is defined as "Mayo score improvement". In addition, the Mayo score defines "mucosal healing" when the subscore of endoscopic features is 0 or 1.

The assessment value of the pathological examination is an assessment value in which a physician or the like determines the grade of the pathological conditions based on the diagnosis result of the pathological examination including biopsy of the affected site. The assessment value for the pathological examination may be an assessment value obtained by any known scoring method.

For example, the assessment value of the pathological examination can be determined by using the Geboes score of biopsy histological findings. The Geboes score is a commonly used index for scoring the pathological findings of ulcerative colitis. Specifically, Geboes scores are assessments based on the definitions illustrated in Table 6 below.

TABLE 6

| Grade | Definition |
|---|---|
| Grade 0 | Structural change alone, no increased infiltration of chronic inflammatory cells (Lymphocyte or plasma cells). |
| Grade 1 | Infiltration of chronic inflammatory cells (Lymphocyte or plasma cells) in lamina propria. |
| Grade 2 | Infiltration of neutrophils and eosinophils in lamina propria. |
| Grade 3 | Infiltration of neutrophils in epithelium. |
| Grade 4 | Crypt destruction. |
| Grade 5 | Erosion and ulceration. |

The Geboes score is a 6-grade assessment from 0 to 5. However, when it is sufficient to determine the presence or absence of inflammation, the assessment derivation unit 124 may derive assessment values in which Grades 0 to 2 are determined as no findings (no inflammation), while Grades 3 to 5 are determined as the state having pathological inflammation.

The determiner is generated by machine learning. Specifically, the determiner is generated in machine learning by using a large number of affected site images together with at least one or more of a physician's assessment for the affected site images by visual inspection of the affected site or an assessment by a pathological examination. By learning at least 10,000 affected site images and their assessments in machine learning, it is possible to make a determination with an accuracy having a difference being substantially the same level of difference in the assessment values among a plurality of physicians. For example, the determiner may be generated by machine learning using a deep neural network.

For example, since it is difficult to perform assessment on a disease such as ulcerative colitis by visual inspection of the affected site, assessments performed by physicians by visual inspection of an affected site have variations among physicians even when they are specialists. According to the present embodiment, by using a determiner generated by machine learning, it is possible to make a diagnostic assessment of a disease such as ulcerative colitis without a specialist. In addition, by using a determiner generated by machine learning, it is possible to avoid assessment variation among physicians, enabling treatment on patients based on assessment values obtained by assessment based on more objective and reproducible criteria.

Meanwhile, pathological examination has a possibility of damaging the patient and a risk of inducing complications in the patient during tissue collection. Furthermore, due to a limited number of pathologists who perform pathological examinations, pathological examinations can be performed at limited locations, leading to a prolonged time to make a diagnosis. In addition, pathological examination would incur additional costs for the patient. According to the present embodiment, by using the determiner generated by machine learning, it is possible to derive the result of the pathological examination without tissue collection, leading to suppression of occurrence of physical, temporal, and financial burden on the patient. Moreover, since the result of the pathological examination is a definitive diagnosis, the determiner generated by machine learning can derive the assessment by the pathological examination with higher accuracy.

In the present embodiment, the determiner may be generated by performing machine learning of data in which a large number of affected site images are associated with parameters other than the assessment described above. For example, the determiner may be generated by performing machine learning of a large number of affected site images and a dosage or treatment methods for the patient who provides the affected site images.

The assessment derivation unit 124 derives assessment item-based tile assessment values, as the tile assessment value. For example, the assessment items may be items of bleeding, tumor, or visible vascular pattern of the affected site, and may be items of pathological examination. Furthermore, the assessment derivation unit 124 may calculate a tile assessment value including a mixture of individual assessment items. For example, tile assessment values may be derived by using at least two or more assessment values of bleeding, ulcer, or visible vascular pattern of the affected site. For example, in this case, tile assessment values may be determined by totaling at least two or more assessment values of bleeding, ulcer, or visible vascular pattern of the affected site.

The assessment derivation unit 124 calculates the reliability of each of tile assessment values, in addition to the tile assessment value. The reliability is a value indicating the certainty of the tile assessment value, and can be expressed by a probability or a numerical value of 0 to 1 (for example, 1 has a highest certainty). The assessment derivation unit 124 may judge that the tile assessment value is reliable when the reliability is a threshold or more and may output the reliability to the display device 130 described below. In contrast, when the reliability is less than the threshold, the assessment derivation unit 124 may judge that the tile assessment value is unreliable and does not have to output the tile assessment value to the display device 130 described below, or may output a result indicating non-analyzable to the display device 130.

The assessment derivation unit 124 estimates the overall assessment value regarding a whole of an affected site image based on the tile assessment value. This enables the user to assess the overall affected site image instead of a part of the image, making it possible to make a more accurate diagnosis for an ulcerative disease.

Specifically, the overall assessment value may be derived as an average assessment value obtained by averaging the tile assessment values of the tile images included in the affected site image. However, when assessing an assessment item such as bleeding, which is characterized by the presence or absence of occurrence rather than the degree of pathological condition, the assessment derivation unit 124 may derive the overall assessment value by weighting the bleeding site. In such a case, the assessment derivation unit 124 may derive the overall assessment value by using a maximum value of the tile assessment values instead of, or in addition to, the average of the tile assessment values.

Furthermore, the assessment derivation unit 124 may derive the overall assessment value by further using the probability distribution of the tile assessment value. For example, the derivation device 120 may derive the overall assessment value in consideration of the degree of dispersion, standard deviation, or the like of the tile assessment value.

Furthermore, the assessment derivation unit 124 may select a tile image to be used for estimating the overall assessment value from a plurality of tile images based on the luminance of each of the tile images. According to this derivation, the assessment derivation unit 124 can exclude the tile image containing noise, over-illumination, shadow, or the like, which makes it difficult to derive the tile assessment value, from the affected site image.

Specifically, the assessment derivation unit 124 may use a tile image whose luminance is a first threshold or more and a second threshold or less for estimating the overall assessment value. The second threshold represents a luminance threshold higher than the first threshold. These thresholds can be appropriately determined by the user or the like. With this configuration, the assessment derivation unit 124 can exclude the tile image whose luminance is too high by the second threshold and can exclude the tile image whose luminance is too low by the first threshold. Therefore, the assessment derivation unit 124 can increase the reliability of the derived tile assessment value, leading to achievement of estimation of the overall assessment value with higher reliability.

The display device 130 presents at least one of the tile assessment value or the overall assessment value to the user. The display device 130 may be, for example, a touch panel type display, a three-dimensional display, a spatial display, a projection type display, or the like. Specifically, the display device 130 may be any of a Cathode Ray Tube (CRT) display, a liquid crystal display, a plasma display, an electroluminescence (EL) display, a laser projector, an LED projector, a lamp, or the like.

Figure 4:
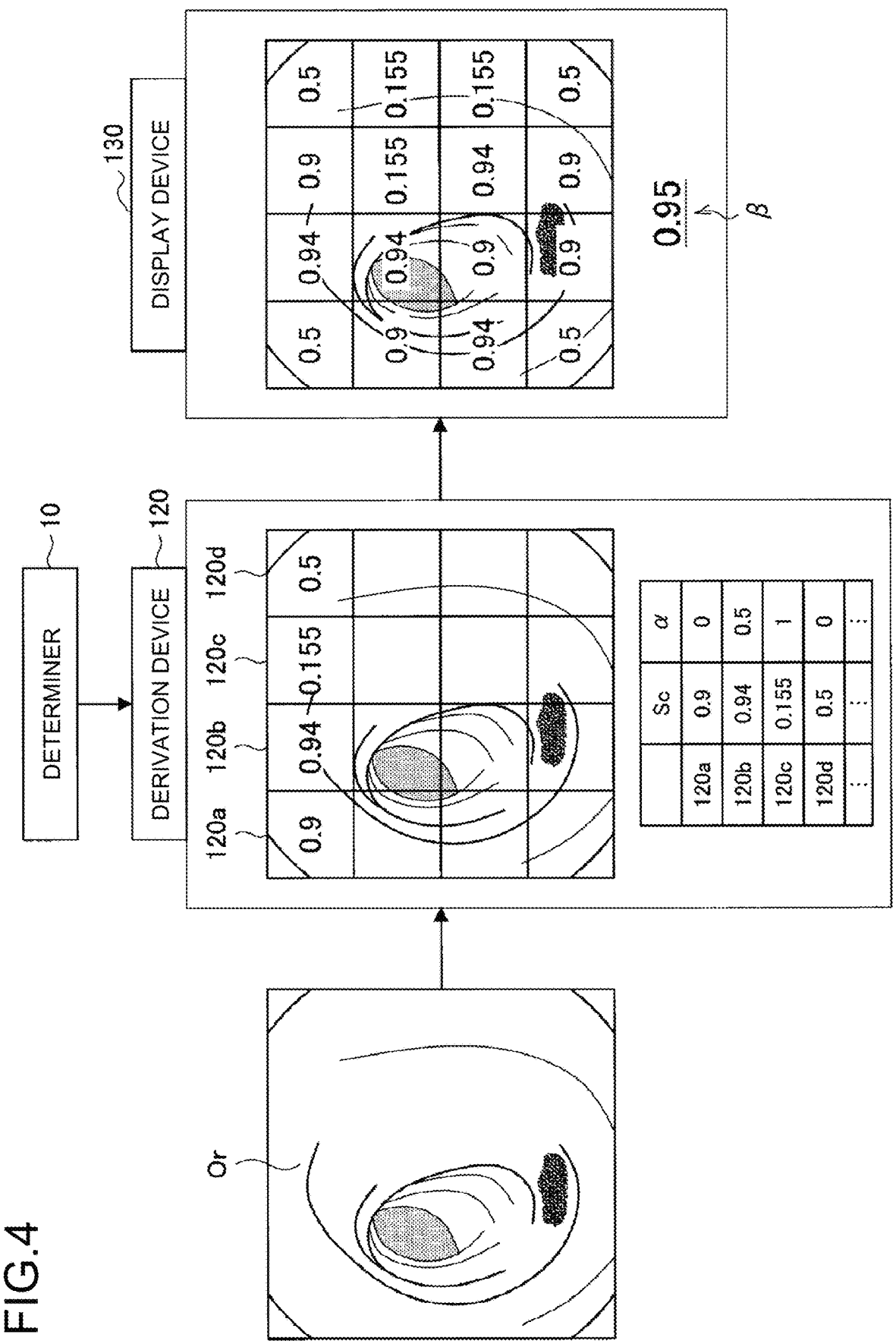
FIG. 4 is a schematic diagram illustrating an example of an operation of the medical support system according to the same embodiment.

Here, operations of the derivation device 120 and the display device 130 will be described in detail with reference to FIG. 4. FIG. 4 is a schematic diagram illustrating operations of the derivation device 120 and the display device 130.

As illustrated in FIG. 4, the derivation device 120 acquires an affected site image Or from the endoscope 110. The derivation device 120 cuts out an affected site image as grid-like images, such as a tile image 120a, a tile image 120b, a tile image 120c, a tile image 120d, and so on by the cut-out unit 122. FIG. 4 illustrates an affected site image cut out as 4×4 (=16) tile images. The assessment derivation unit 124 derives a tile assessment value Sc and reliability α for each of these tile images 120a to 120d by using the determiner 10.

As illustrated in FIG. 4, for example, the tile image 120a has derived values of the tile assessment value Sc as 0.9 and the reliability α as 0. Similarly for other tile images, the tile image 120b has derived values as the tile assessment value Sc of 0.94 and the reliability α of 0.5, the tile image 120c has derived values of the tile assessment value Sc of 0.155 and the reliability α of 1, and the tile image 120d has derived values as the tile assessment value Sc of 0.5 and the reliability α of 0. The assessment derivation unit 124 further derives an overall assessment value β derived from individual tile images.

The display device 130 acquires the above tile assessment values and the overall assessment value β and presents the values to the user. In the display device 130, by superimposing different displays over the affected site image based on the tile assessment value, it is possible to demonstrate the distribution of the assessment of the pathological conditions in the affected site image. For example, the display device 130 may change the color of the tile image in accordance with the tile assessment value of the tile image. Furthermore, the display device 130 may change the transparency of the tile image in accordance with the reliability of the tile assessment value of the tile image.

Figure 5:
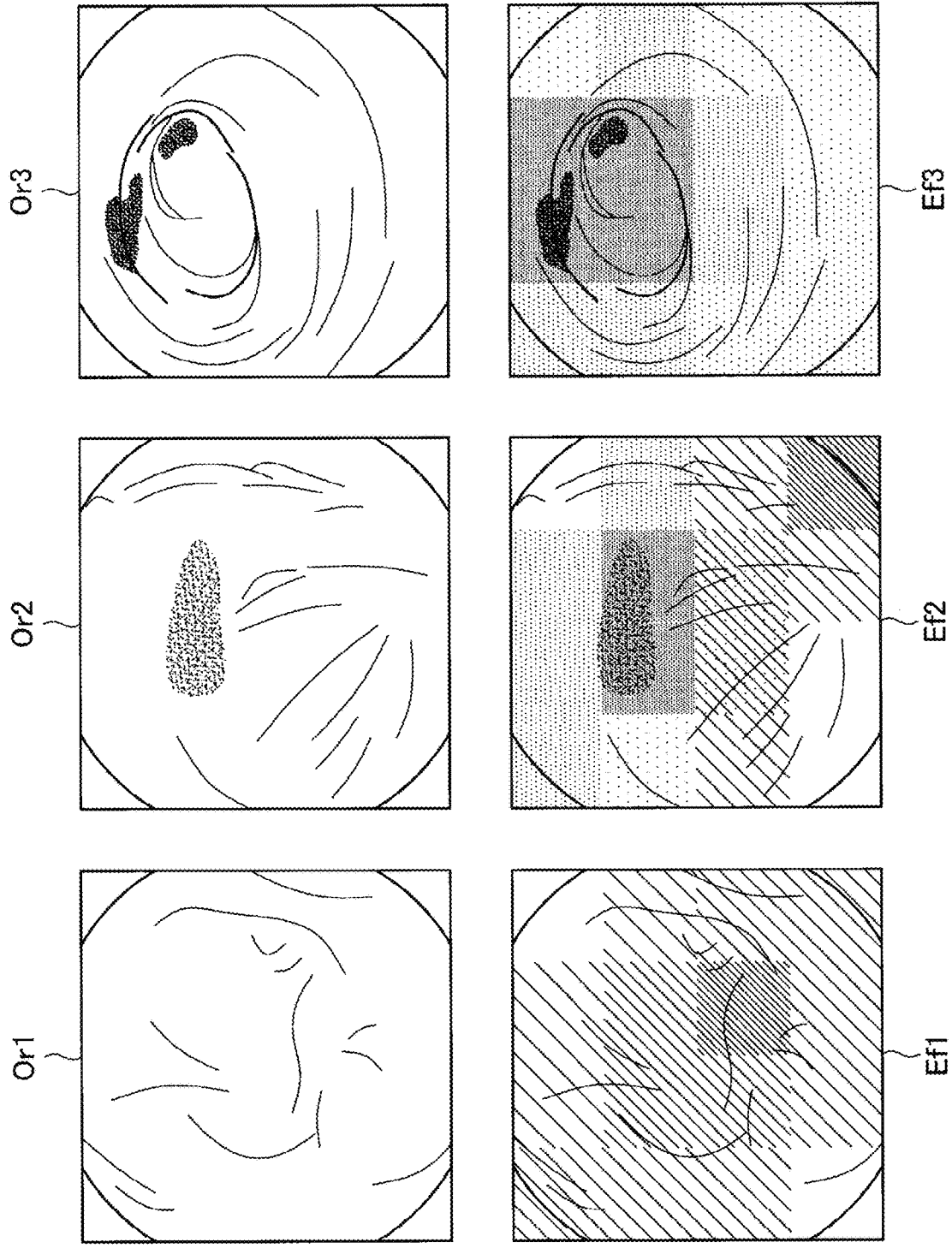
FIG. 5 is a diagram illustrating an example of a display according to the same embodiment.

Modes of display superimposed over the tile image will be further described with reference to FIG. 5. FIG. 5 illustrates an example of display modes superimposed over the tile image. An affected site image Or1 is an image indicating a generally good pathological condition, an affected site image Or2 is an image including a range indicating good pathological condition and a range indicating a poor pathological condition, and an affected site image Or3 is an image generally indicating a poor pathological condition. The tile assessment value Sc (that is, good or poor pathological condition) is presented in a different display mode. For example, the tile assessment value Sc can be presented in different colors or the like (like in heat maps), while the reliability α of the tile assessment value can be presented by the transparency of the color, for example. In FIG. 5, in images Ef1 to Ef3 illustrating the tile assessment values, different colors are represented by different hatch types (that is, diagonal lines or dot hatches), and the transparency of each of colors is represented by the density of each of hatches.

Although the display example of the assessment value and the overall assessment value of the tile image has been described above with reference to FIGS. 4 and 5, the display example is not limited to the display example illustrated in FIGS. 4 and 5. For example, as illustrated in FIG. 2, the display device 130 may display both the affected site image Or and an affected site image in which the assessment values are superimposed and displayed for each of assessment items. With this display, the user (physician) can visually inspect the images Ef1 to Ef3 indicating the tile assessment values of each of assessment items while visually inspecting the actual affected site images Or1 to Or3. Therefore, the user can examine the patient while considering the assessment by the medical support system 1000 and the assessment of the pathological conditions by the user.

2.2. Operation Flow

Figure 6:
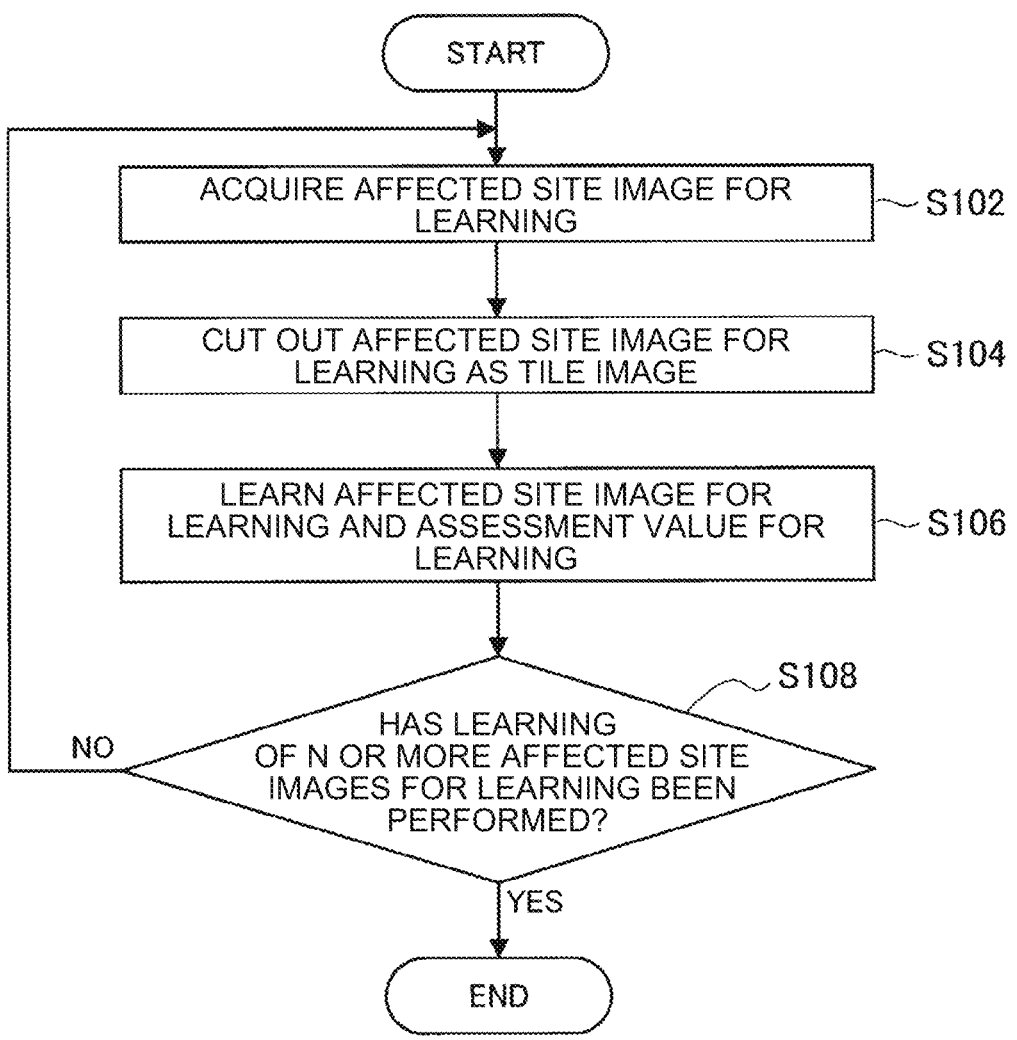
FIG. 6 is a flowchart illustrating an example of an operation flow of the medical support system according to the same embodiment.
Figure 7:
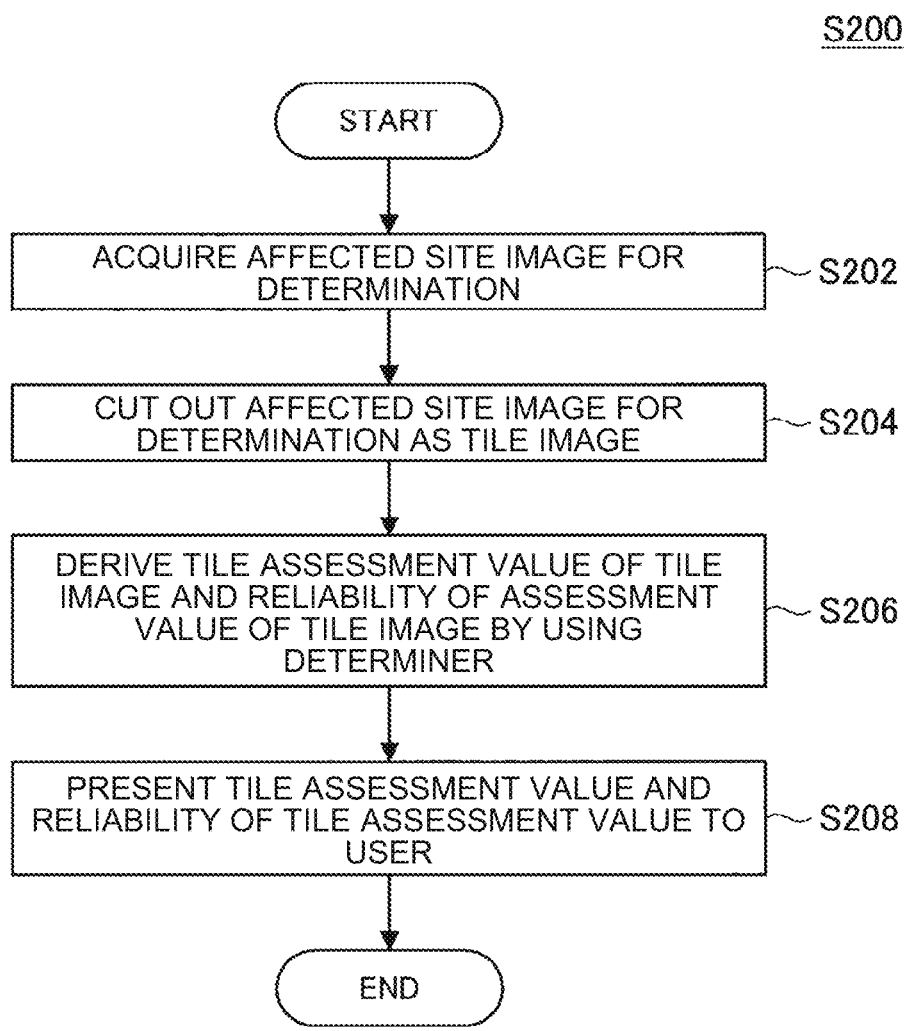
FIG. 7 is a flowchart illustrating an example of an operation flow of the medical support system according to the same embodiment.

Here, with reference to FIGS. 6 and 7, an example of a determiner generation flow S100 for generating the determiner in the medical support system 1000 and an example of an overall operation flow S200 of the medical support system 1000 will be described.

The determiner generation flow S100 will be described with reference to FIG. 6.

First, the derivation device 120 acquires an affected site image for learning (S102).

Next, the affected site image for learning is cut out as a tile image (S104). The tile image may be cut out in a fixed shape or may be cut out in a random shape.

Next, the affected site images for learning cut out as tile images, and assessment values for the affected site image, are fed for the learning (S106). The assessment value for the affected site image is an assessment value judged by a physician or the like, and includes an assessment by a physician's visual inspection of the affected site, an assessment based on the result of a pathological examination, or the like.

Next, it is judged whether learning of N or more affected site images for learning has been performed (S108). When the learning of N or more affected site images for learning has not been performed (S108/No), the learning of the affected site image is repeated until the operation reaches the learning of N or more images. The affected site image for learning that is used for machine learning may be subjected to data augmentation by rotation, enlargement, reduction, deformation, or the like. By using at least 10,000 affected site images for learning, a highly reliable determiner can be generated.

Hereinabove, the determiner generation flow S100 has been described.

Next, with reference to FIG. 7, the overall operation flow S200 of the medical support system 1000 using the determiner will be described.

First, the derivation device 120 acquires an affected site image for determination by using the endoscope 110 or the like (S202). The affected site image may be a moving image being monitored by the endoscope 110, or may be a still image captured by the endoscope 110.

Next, the cut-out unit 122 cuts out the affected site image for determination as a tile image (S204). The tile image may be cut out in a fixed shape or may be cut out in a random shape.

Next, the derivation device 120 derives the tile assessment value of the tile image and the reliability of the tile image by using the generated determiner (S206). When deriving the tile assessment value, the derivation device 120 may further derive the overall assessment value for the whole of the affected site image. For example, the derivation device 120 may derive the overall assessment value from the mean value of the tile assessment values in the affected site image, or may derive the overall assessment value from a combination of the maximum value and the mean value of the tile assessment values. Furthermore, the derivation device 120 may further combine the probability distributions of the tile assessment values to derive the overall assessment value. For example, the derivation device 120 may derive the overall assessment value in consideration of the degree of dispersion, standard deviation, or the like of the tile assessment value.

Thereafter, the display device 130 presents the tile assessment value of the tile image and the reliability of the tile assessment value to the user (S208). The display device 130 may further display the overall assessment value.

The overall operation flow of the medical support system 1000 has been described as above. According to the medical support system 1000 that performs these operations, the physician 1 can make a diagnosis of the pathological condition with higher confidence in consideration of the assessment of the affected site derived by the medical support system 1000 and the diagnosis of the physician 1.

3. Modification

Figure 8:
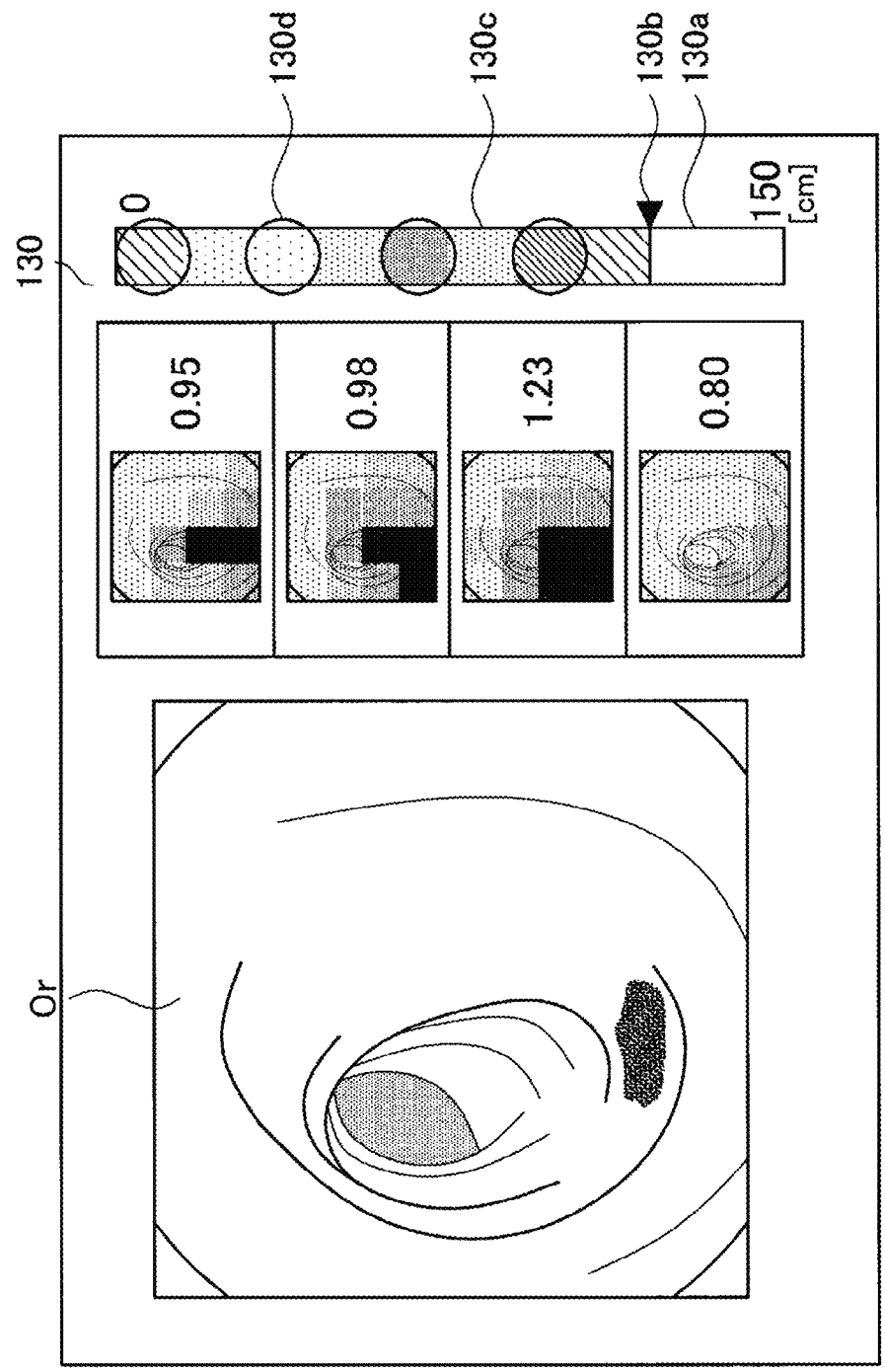
FIG. 8 is a diagram illustrating a modification of the display according to the same embodiment.

A modification of the display to be displayed on the display device 130 will be described with reference to FIG. 8. FIG. 8 is a diagram illustrating a modification of the display that is displayed on the display device 130. In the above embodiment, the display device 130 displays the affected site image in which the assessment value of each of items is presented together with the affected site image Or. By contrast, in the present modification, together with the assessment image in which the tile assessment value of each of items is presented, the display device 130 further displays the position of the endoscope 110 in the patient's body and overall assessment values corresponding to the position of the endoscope 110.

As illustrated in FIG. 8, for example, the display device 130 may display a display bar 130*a* indicating the position of the endoscope in a range from one end to the other end of a display region of the display device 130. The display bar 130*a* indicates the length of an examined portion by the portion from one end to the other end in the longitudinal direction. For example, when the diagnosis is for colonoscopy, the display bar 130*a* may have a setting in which one end of the display bar 130*a* indicates 0 cm at an insertion start point (for example, anus) of the endoscope, and the other end of the display bar 130*a* indicates an end point (for example, 150 cm) of the colonoscopy. A position 130*b* of the endoscope in the large intestine at the time of examination may be expressed by an insertion length corresponding to the longitudinal direction of the display bar 130*a*.

Furthermore, the display bar 130*a* may include a range 130*c* in which the color changes continuously. Specifically, the display bar 130*a* may be displayed in a color that changes with each of overall assessment values of the display bar 130*a*. Furthermore, the display bar 130*a* may display the position having a characteristic overall assessment value with highlighting with a marking 130*d*. For example, the position determined to have a high overall assessment value from the start to the end of the endoscopic examination may be highlighted in display by the marking 130*d*. The marking 130*d* may be attached to a portion selected by the user or the like.

Alternatively, the display device 130 may use enlarged display for a portion having a high tile assessment value in the affected site image. With these display methods, the medical support system 1000 can present to the user the portion judged to have particularly poor pathological conditions with emphasized manner.

4. Examples

Hereinafter, the determiner generated by the medical support system according to the present embodiment will be described more specifically with reference to examples. The examples illustrated below are one condition example for illustrating the feasibility and effects of the medical support system according to the present embodiment, and the technology according to the present disclosure is not limited to the following examples.

(Background)

It is important that ulcerative colitis have objective assessment by using endoscopic and histological assessments. However, the assessment of ulcerative colitis has variation within and between observers due to individual differences in experience. Therefore, in order to implement consistent and objective assessment in real time for ulcerative colitis, the present example aims to develop a deep neural network for assessment of UC (DNUC) based on endoscopic images.

Specifically, objective observation is key to the management of patients with ulcerative colitis (hereinafter, also referred to as UC).

For example, past studies have demonstrated that endoscopic assessment can predict the clinical outcome of UC. Therefore, there are increasing cases where endoscopic assessment is used for assessment and management of UC patients with a therapeutic goal of endoscopic remission. However, since endoscopic observation requires training, endoscopic assessment might have a difference depending on the endoscopist.

On the other hand, histological remission has been proposed as another therapeutic goal with which clinical outcome is predictable. For example, in the case of patients having minimal residual acute inflammation, the disease is more likely to recurrent, and thus, histological remission without residual acute inflammation can be set as an ultimate therapeutic goal. The histological assessment of judging histological remission is an important assessment. However, this assessment requires a mucosal specimen and may have various interpretations depending on the pathologist.

In this manner, the specialist's assessment of the endoscopic image or the mucosal specimen is subjectively interpreted based on the individual's experience, making it difficult to make a generalized assessment and a real-time characteristic assessment.

Here, in recent years, there have been reports pointing out the role of artificial intelligence (AI) using deep learning in various medical fields. A deep neural network (DNN) is an AI machine learning method that constructs a deep learning architecture. The present example has developed a DNN system of UC (DNUC) that implements a consistent and objective endoscopic and histological assessment by constructing a DNN using UC endoscopic images. Furthermore, the accuracy of the developed DNUC was assessed by a verification test.

(Outline)

The present example includes two stages, a development stage and a verification stage. A DNUC was developed using past endoscopic images and biopsy specimens in the development stage; the validity of the DNUC was examined on new test data in the verification stage.

In the development stage, a DNUC algorithm (that is, determiner) was constructed by re-examining 20149 colonoscopic images obtained from 1000 patients and 3285 biopsy specimens.

During the verification stage, new test data was collected to assess the accuracy of the DNUC algorithm. In the assessment of ulcerative colitis, the case where the Ulcerative Colitis Endoscopic Index of Severity (UCEIS) is 0 is defined as endoscopic remission, and the case where the Geboes assessment value (score) was 3 or less is defined as histological remission. Specifically, in the verification stage, 2400 endoscopic images and 2317 biopsy specimens were obtained from 500 enrolled patients, and assessment is performed regarding determination accuracy of endoscopic and histological remission in the DNUC and the degree of agreement with specialists. As described in detail below, DNUC demonstrated high diagnostic accuracy (90.1%) and high consistency in determination of endoscopic remission. The kappa correlation coefficient between DNUC and the endoscopist in the determination of endoscopic remission was 0.785. In addition, DNUC indicated high diagnostic accuracy (90.9%) in the determination of histological remission. The kappa correlation coefficient between DNUC and biopsy results in the determination of histological remission was 0.748.

(Patients)

At the development stage, past endoscopic images and biopsy specimens were obtained by re-examining a series of cases of UC patients who underwent colonoscopy at Tokyo Medical and Dental University Medical Hospital. In the verification stage, pieces of new test data were obtained by enrolling patients who underwent colonoscopy for the treatment of UC at the same hospital from April to November 2018. Regarding the use of data in the development stage, consent was obtained from all patients by the opt-out method. In addition, in the verification stage, written informed consent was obtained from all patients.

However, patients who meet the following exclusion criteria were excluded.

(1) Patients with a history of colon resection, or have inflammatory bowel disease, Crohn's disease, colon/rectal neoplasm, or intestinal concomitant infection for which no certain diagnosis has been made.

(2) Patients who are contraindicated for colonoscopy.

(3) Patients contraindicated for biopsy due to blood disease or antithrombotic/anticoagulant therapy.

In addition, for all patients, the degree of disease was judged based on the Montreal classification, and clinical activity was judged using the partial Mayo score or assessment value. All patients underwent standard intestinal pretreatment with Nifrec or Mobiprep (EA Pharma Co., Ltd.) and the status of intestinal irrigation was also recorded.

(Endoscopy Procedure and Assessment)

A colonoscopic mucosal image (image size 4.5 MB) was captured by examination with a standard colonoscope (Olympus Medical Systems Corp.). In general colonoscopy, pigment endoscopy is performed after white light examination. However, the images used in the present example is white light images alone.

The Ulcerative Colitis Endoscopic Index of Severity (UCEIS) was used to assess the endoscopic severity of ulcerative colitis. Specifically, the UCEIS assessment value was obtained in the total value range of 0 to 8 simply calculated by summing the visible vascular pattern (assessment value 0 to 2), bleeding (assessment value 0 to 3), and erosions and ulcers (assessment value 0 to 3), in which the UCEIS assessment value 0 was defined as endoscopic remission. Although the UCEIS typically scores the assessment value in the disease region with the highest severity, the present example obtains the assessment values based on all the captured endoscopic images.

(Histological Assessment)

A biopsy specimen were collected from the patient's colonic mucosa. The Geboes assessment value (score) was used in the assessment of the histological severity of inflammation of ulcerative colitis, in which the case of Geboes assessment values (scores) of 3 or less were defined as histological remission.

(Development Stage)

A dataset was prepared for use in training and constructing the DNUC. Specifically, as described above, a total of 20149 images of colonoscopy performed on 1000 patients from July 2015 to March 2018 were collected. Also collected 3285 were biopsy specimens (already sampled) from these patients. Note that endoscopic images of regions where tissue biopsy had not been performed were excluded.

The UCEIS assessment values of all images were assessed by one endoscopist (having 11 years of IBD endoscopy history), while the histological activity of all mucosal specimens was assessed by one pathologist (having 13 years of IBD pathology history). Neither the endoscopist nor the pathologist is informed about the test results of the other party.

Here, the UCEIS assessment value and the number and percentage of histological data (percentage (%) in parentheses) are illustrated in Table 7 below. Histological data are linked to endoscopic images of the region where the tissue biopsy was performed.

TABLE 7

| Endoscopic data (20149 images) | 0 | 1 | 2 | 3 | 4 | 5 | 6 | 7 | 8 |
|---|---|---|---|---|---|---|---|---|---|
| UCEIS total evaluation value | 9135 (45.3) | 2859 (14.2) | 1293 (6.4) | 1508 (7.5) | 1890 (9.4) | 1990 (9.9) | 1041 (5.2) | 385 (1.9) | 48 (0.0) |
| UCEIS partial evaluation value (vascular pattern) | 9458 (46.9) | 5079 (25.2) | 5612 (27.9) | | | | | | |
| UCEIS partial evaluation value (bleeding) | 13195 (65.5) | 5596 (27.8) | 1000 (5.0) | 358 (1.8) | | | | | |
| UCEIS partial evaluation value (erosions and ulcers) | 12799 (63.5) | 3561 (17.7) | 3097 (15.4) | 692 (3.4) | | | | | |
| Histological data (3285 biopsy specimens) | Remission (Geboes evaluation value: 3 or less) 1848 (56.3) | | | | Active (Geboes evaluation value: over 3) 1437 (43.7) | | | | |

The captured endoscopic images were input to DNUC so as to train the DNUC on the endoscopic image and assessment value (UCEIS assessment and histological assessment). The DNUC was also designed to output results for endoscopic remission (achieved/not achieved), histological remission (achieved/not achieved), and UCEIS assessment values. In order to achieve accurate output, the DNUC cutoff was set to 85% or more, and images not meeting the cutoff were judged to be "unanalyzable". In order to achieve more accurate output, another cutoff of DNUC was set to 95% or more, and an image satisfying this cutoff was judged to be "highly confident".

The learning of the DNUC was performed as follows.

First, an original 1080×1080 pixel endoscopic image was divided into 299×299 pixel square tiles. Next, by calculating an average luminance value of the divided square tiles, the effects of overexposure and the dark areas were removed, so as to achieve selection of the tiles applicable to DNUC learning. The square tiles were then subjected to data augmentation including random rotation from 0 to 359 degrees, scaling (enlargement/reduction) from 0.8 to 1.2 times, inversion, or shearing from 0.8 to 1.2 times.

Thereafter, the DNUC is constructed by applying a latest DNN architecture, Inception v3 model (https://arxiv.org/abs/1512.00567). Specifically, the final layer of the Inception model was altered, and the softmax activation function was used to classify each of assessment values. The Inception model was trained with 2000×10 epochs to obtain the probability of each of assessment values. Furthermore, all the results of 299×299 pixel square tiles derived from the same original image were averaged and scored.

The output result from the DNUC can be presented to the user, for example, by creating a superposed image in which the tiles are colored with a specific translucent color based on the original endoscopic image. The fill color and transmittance can be determined based on the result and probability of the assessment value.

(Verification Stage)

A new test dataset was collected to assess the diagnostic accuracy of the DNUC that had been constructed. Specifically, colonoscopy is performed on all of the above-described patients, in which endoscopic images of five colon sites (ascending colon, transverse colon, descending colon, sigmoid colon, and rectum) are captured and five mucosal biopsy specimens were collected from the five corresponding portions. Colonoscopy was performed by seven different endoscopists.

However, severely ill UC patients were examined under limitation of sigmoidoscopy or a limited number of biopsy specimens. The endoscopic images were assessed by the same endoscopist as in the development stage. 400 biopsy specimens of mild to moderate UC patients were assessed by the same pathologist as in development stage, while the remaining biopsy specimens were assessed by another uninformed pathologist.

Results of the DNUC were output for each of endoscopic images. The output results were compared with endoscopic and histological data to assess the DNUC by the following assessment items.

(1) As primary assessment items (endpoints), the accuracy of DNUC when assessing endoscopic remission and the accuracy of DNUC when predicting histological remission are set.

(2) As secondary assessment items (endpoints), DNUC's capability of determining UCEIS, DNUC accuracy in endoscopic and histological remissions of each of colon sites, DNUC accuracy in cases with high confidence, and DNUC accuracy for the layered cases due to intestinal irrigation states.

Statistical Analysis

Figure 9A:
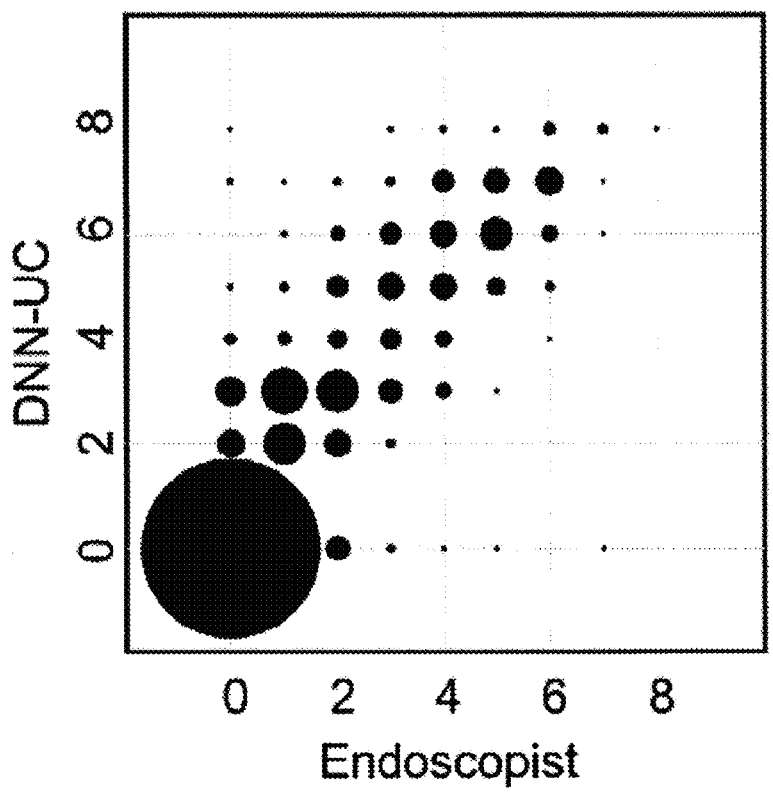
FIG. 9A is a scatter plot illustrating a correlation between an endoscopist and DNUC when scoring UCEIS for cases judged to be analyzable.
Figure 9B:
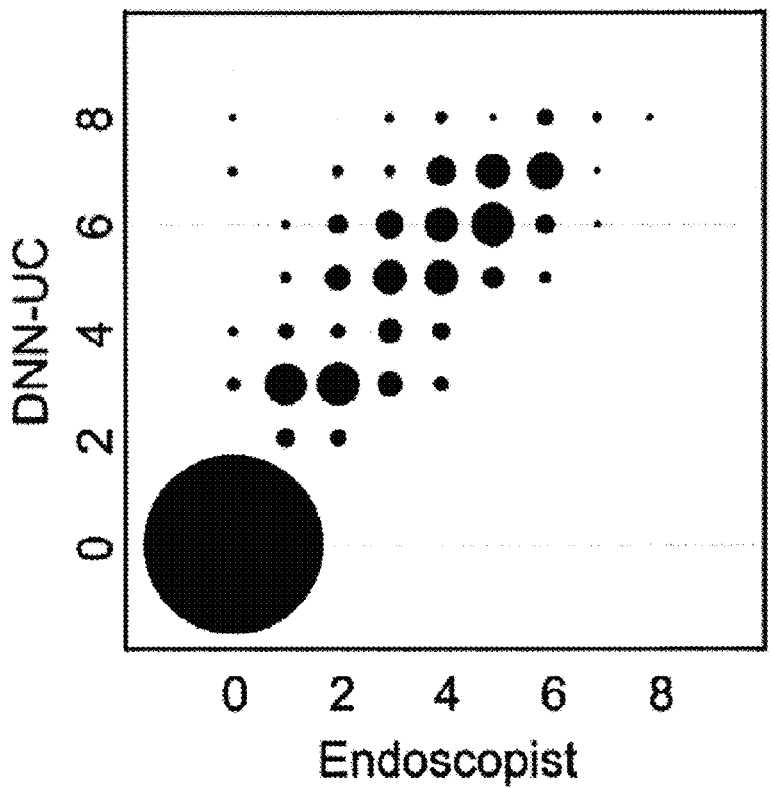
FIG. 9B is a scatter plot illustrating a correlation between an endoscopist and DNUC when scoring UCEIS for cases judged to be highly confident.

Here, a small-scale pilot test using 500 images estimated that at least 10,000 images were required in the development stage and at least 1000 images were required in the verification stage. Accordingly, the diagnostic accuracy of DNUC is determined by comparing the output result of DNUC with the data assessed by specialists (endoscopist and pathologists), and then, the degree of agreement between DNUC and specialists, in endoscopic and histological remissions, was calculated by using the kappa correlation coefficient. In addition, the correlation between specialists and DNUC at the time of scoring UCEIS was judged by an intraclass correlation coefficient (ICC) (FIGS. 9A and 9B). The statistical analysis used SPSS version 21.0 (IBM).

(Endoscopic and Histological Results on Patients)

At the verification stage, 500 patients were enrolled. The clinical features of the enrolled patients are illustrated in Table 8 below.

TABLE 8

| | Variable | All patients (n = 500) |
|---|---|---|
| | Sex Male/Female (%) | 280 (56.0%)/220 (44.0%) |
| | Median age (year) (range) | 41 (15-81) |
| | Median disease period (year) (range) | 7 (0.5-43) |
| Instruction of colonoscopy n (%) | Disease activity assessment | 298 (59.6%) |
| | Cancer screening | 202 (40.4%) |
| Disease location n (%) | Proctitis | 42 (8.4%) |
| | Left colitis | 117 (23.4%) |
| | Pan-colitis | 341 (68.2%) |
| Partial Mayo evaluation value n (%) | Stool frequency (0/1/2/3) | 271 (54.2%)/95 (19.0%)/62 (12.4%)/72 (14.4%) |
| | Rectal bleeding (0/1/2/3) | 333 (66.6%)/101 (20.2%)/61 (12.2%)/5 (1.0%) |
| | Physician's global assessment (0/1/2/3) | 314 (62.8%)/101 (20.2%)/75 (15.0%)/10 (2.0%) |
| | Median Hb (g/dl) (range) | 13.7 (6.5-19.2) |
| | Median C-reactive protein (mg/dL) (range) | 0.7 (0.1-390) |
| Combination Therapy n (%) | 5-Aminosalicylic acid oral preparation | 436 (87.2%) |
| | Immunomodulator | 181 (36.2%) |
| | Steroid | 51 (10.2%) |
| | Anti-TNF inhibitor | 89 (17.8%) |
| | Local treatment with 5-Aminosalicylic acid | 106 (21.2%) |
| | Local treatment with steroid | 89 (17.8%) |

As illustrated in Table 8, 298 (59.6%) patients were instructed to have a colonoscopy to assess disease activity, and 202 (40.4%) patients were instructed to have a colonoscopy for cancer screening. A total of 42 patients have not undergone total colonoscopy, based on the endoscopist's judgment regarding the risk of complications. In addition, there were less than four biopsy specimens in 60 patients.

From these patients, 2400 endoscopic images and 2317 biopsy specimens were obtained. Table 9 below illustrates the results of assessment of the obtained endoscopic images and biopsy specimens performed by specialists (endoscopists and pathologists).

TABLE 9

| Endoscopic data (2400 images) | 0 | 1 | 2 | 3 | 4 | 5 | 6 | 7 | 8 |
|---|---|---|---|---|---|---|---|---|---|
| UCEIS total evaluation value | 1461 (60.9) | 356 (14.8) | 119 (8.3) | 112 (4.6) | 113 (4.7) | 92 (3.8) | 58 (2.4) | 8 (0.3) | 1 (0.0) |
| UCEIS partial evaluation value (vascular pattern) | 1527 (63.6) | 530 (22.1) | 343 (14.3) | | | | | | |
| UCEIS partial evaluation value (bleeding) | 1998 (83.3) | 344 (14.3) | 47 (2.0) | 11 (0.5) | | | | | |
| UCEIS partial evaluation value (erosions and ulcers) | 1925 (80.2) | 269 (11.2) | 160 (6.7) | 46 (1.9) | | | | | |
| Histological data (2317 biopsy specimens) | Remission (Geboes evaluation value: 3 or less) 1779 (76.8) | | | | Active (Geboes evaluation value: over 3) 538 (23.2) | | | | |

As illustrated in Table 9, 60.9% of the images were judged to be endoscopic remission and 76.8% of the specimens were judged to be histological remission. Most of the mucosal specimens judged to be moderate to severe (UCEIS assessment value 3 or higher) by endoscopy were judged to be histologically active. The judged mucosa with a UCEIS assessment value of 0, 1 or 2 was judged to be histological remission with percentages of 98.5% (1,417 of 1438), 78.3% (271 of 346), and 41.8% (79 of 189), respectively.

(Assessment of DNUC's Endoscopic Assessment Value)

In the endoscopic assessment values, 92.4% of the images were judged to be "analyzable" while 50.7% of the images were judged to be "highly confident" by DNUC.

Regarding the above-described primary assessment items (endpoints), as illustrated in Table 10 below, DNUC indicated high sensitivity (94.3%), high specificity (83.1%), high positive predictive value (PPV: 90.3%), high negative predictive value (NPV: 89.8%), and high diagnostic accuracy (90.1%) in determining endoscopic remission. In addition, the kappa correlation coefficient between DNUC and endoscopists in endoscopic remission was 0.785. That is, the accuracy of DNUC in assessing the mucosal inflammation in UC patients was comparable to the accuracy of the endoscopists.

TABLE 10

| Endoscopic Remission (2400 images) | Number of Pixels (%) | Sensitivity (95% CI) | Specificity (95% CI) | PPV (95% CI) | NPV (95% CI) | Accuracy (95% CI) | kappa correlation coefficient (95% CI) |
|---|---|---|---|---|---|---|---|
| Analyzable | 2218 (92.4%) | 94.3% (93.3%-95.2%) | 83.1% (81.4%-84.6%) | 90.3% (89.3%-91.1%) | 89.8% (87.9%-91.4%) | 90.1% (88.8%-91.2%) | 0.785 (0.758-0.810) |
| Highly confident | 1216 (50.7%) | 98.8% (98.2%-99.2%) | 98.5% (97.4%-99.1%) | 99.1% (98.4%-99.5%) | 98.0% (97.0%-98.7%) | 98.7% (97.9%-99.2%) | 0.972 (0.955-0.983) |

In addition, regarding the above-described secondary assessment item (endpoint), the ICC between the specialist and DNUC at the time of scoring UCEIS was 0.861, as illustrated in FIG. 9A. In high-confidence cases in particular, DNUC indicated very high accuracy (98.7%) and high consistency (kappa correlation coefficient of 0.972), as illustrated in FIG. 9B. The accuracy and consistency of DNUC was acceptable, but the accuracy of DNUC in the rectum was relatively low, as illustrated in Table 11 below. In addition, as illustrated in Table 12 below, the accuracy of DNUC was low also when the assessment value of intestinal irrigation was "poor" to "failing".

TABLE 11

| Endoscopic Remission (2218 images) | Number of Pixels (%) | Sensitivity (95% CI) | Specificity (95% CI) | PPV (95% CI) | NPV (95% CI) | Accuracy (95% CI) | kappa correlation coefficient (95% CI) |
|---|---|---|---|---|---|---|---|
| Ascending colon | 431 (19.4%) | 99.2% (97.9%-99.7%) | 53.8% (48.0%-56.3%) | 90.7% (89.5%-91.2%) | 93.3% (83.3%-97.7%) | 91.0% (88.8%-91.9%) | 0.635 (0.550-0.671) |
| Transverse colon | 440 (19.8%) | 98.3% (96.8%-99.2%) | 69.2% (63.5%-72.6%) | 92.5% (91.0%-93.3%) | 91.3% (83.7%-95.8%) | 92.3% (89.9%-93.7%) | 0.741 (0.661-0.788) |
| Descending colon | 455 (20.5%) | 95.8% (93.7%-97.3%) | 77.8% (73.2%-81.1%) | 90.3% (88.3%-91.7%) | 89.6% (84.4%-93.4%) | 90.1% (87.2%-92.2%) | 0.763 (0.694-0.813) |
| Sigmoid colon | 460 (20.7%) | 92.6% (89.7%-94.8%) | 86.6% (83.3%-89.1%) | 88.6% (85.9%-90.7%) | 91.2% (87.8%-93.9%) | 89.8% (86.7%-92.1%) | 0.794 (0.733-0.842) |
| Rectum | 432 (19.5%) | 69.5% (64.2%-73.7%) | 94.7% (92.5%-96.5%) | 84.8% (78.2%-89.8%) | 88.1% (86.0%-89.7%) | 87.3% (84.1%-89.7%) | 0.678 (0.597-0.740) |

TABLE 12

| Endoscopic Remission (2218 images) | Number of Pixels (%) | Sensitivity (95% CI) | Specificity (95% CI) | PPV (95% CI) | NPV (95% CI) | Accuracy (95% CI) | kappa correlation coefficient (95% CI) |
|---|---|---|---|---|---|---|---|
| Excellent to Good | 1480 (66.7%) | 94.4% (93.3%-95.3%) | 83.3% (80.8%-85.5%) | 92.8% (91.7%-93.8%) | 86.6% (84.0%-88.9%) | 91.0% (89.5%-92.3%) | 0.785 (0.749-0.817) |
| Passing | 592 (26.7%) | 95.3% (92.9%-97.0%) | 85.3% (82.8%-87.0%) | 86.9% (84.8%-88.5%) | 94.7% (92.0%-96.6%) | 90.4% (88.0%-92.1%) | 0.807 (0.759-0.842) |
| Poor to Failing | 146 (6.6%) | 89.1% (80.4%-924.6) | 74.7% (69.5%-78.1%) | 68.1% (61.4%-72.3%) | 91.9% (85.4%-96.0%) | 80.1% (73.6%-84.3%) | 0.601 (0.470-0.685) |

(Assessment of DNUC's Histological Remission)

In prediction of histological remission by DNUC, 92.0% of the images were judged "analyzable" and 40.9% of the images were judged to be "highly confident".

Regarding the above-described primary assessment items (endpoints), DNUC indicated, in the prediction of histological remission, high sensitivity (92.6%), high specificity (85.0%), high PPV (95.6%), high NPV (76.7%), and high diagnostic accuracy (90.9%), as illustrated in Table 13 below. Furthermore, the kappa correlation coefficient between DNUC and biopsy results in the histological remission was 0.748. That is, DNUC was able to predict histological remission without the need for mucosal biopsy.

TABLE 13

| Histological Remission (2317 images) | Number of Pixels (%) | Sensitivity (95% CI) | Specificity (95% CI) | PPV (95% CI) | NPV (95% CI) | Accuracy (95% CI) | kappa correlation coefficient (95% CI) |
|---|---|---|---|---|---|---|---|
| Analyzable | 2131 (92.0%) | 92.6% (91.9%-93.3%) | 85.0% (82.2%-87.4%) | 95.6% (94.8%-96.3%) | 76.7% (74.2%-78.9%) | 90.9% (89.7%-92.0%) | 0.748 (0.713-0.778) |
| Highly confident | 947 (40.9%) | 97.8% (97.1%-98.3%) | 96.8% (94.6%-98.2%) | 98.8% (98.0%-99.3%) | 94.2% (92.1%-95.5%) | 97.6% (96.4%-98.3%) | 0.938 (0.909-0.957) |

In high-confidence cases, DNUC indicated very high accuracy (97.6%) and high consistency (kappa correlation coefficient 0.938). The accuracy and consistency of DNUC was acceptable for the secondary assessment items (endpoints) described above, but the accuracy and consistency of DNUC in the rectum was relatively low, as illustrated in Table 14 below. In addition, as illustrated in Table 15 below, the accuracy and consistency of DNUC was relatively low also when the assessment value of intestinal irrigation was "poor" to "failing".

TABLE 14

| Histological Remission (2131 images) | Number of Pixels (%) | Sensitivity (95% CI) | Specificity (95% CI) | PPV (95% CI) | NPV (95% CI) | Accuracy (95% CI) | kappa correlation coefficient (95% CI) |
|---|---|---|---|---|---|---|---|
| Ascending colon | 424 (19.9%) | 98.4% (97.4%-99.2%) | 28.6% (19.4%-35.6%) | 92.6% (91.7%-93.3%) | 66.7% (45.2%-83.2%) | 91.5% (89.7%-92.9%) | 0.362 (0.225-0.467) |
| Transverse colon | 412 (19.3%) | 99.2% (98.1%-99.7%) | 65.0% (55.2%-69.8%) | 96.3% (95.3%-96.8%) | 89.7% (76.1%-96.3%) | 95.9% (94.0%-96.8%) | 0.732 (0.608-0.792) |
| Descending colon | 424 (19.9%) | 95.1% (93.4%-96.4%) | 78.9% (71.2%-84.9%) | 95.4% (93.7%-96.7%) | 77.9% (70.3%-83.8%) | 92.2% (89.4%-94.4%) | 0.737 (0.643-0.809) |
| Sigmoid colon | 447 (21.0%) | 92.7% (90.9%-93.8%) | 94.0% (89.7%-96.7%) | 97.3% (95.4%-98.5%) | 84.5% (80.6%-86.9%) | 93.1% (90.5%-94.7%) | 0.839 (0.781-0.877) |
| Rectum | 424 (19.9%) | 69.8% (67.7%-70.6%) | 98.4% (95.6%-99.4%) | 98.3% (95.3%-99.4%) | 71.0% (69.0%-71.8%) | 82.1% (79.7%-83.0%) | 0.651 (0.604-0.667) |

TABLE 15

| Histological Remission (2131 images) | Number of Pixels (%) | Sensitivity (95% CI) | Specificity (95% CI) | PPV (95% CI) | NPV (95% CI) | Accuracy (95% CI) | kappa correlation coefficient (95% CI) |
|---|---|---|---|---|---|---|---|
| Excellent to Good | 1453 (68.3%) | 93.1% (92.3%-93.8%) | 84.5% (80.3%-88.1%) | 96.9% (96.1%-97.6%) | 70.1% (66.6%-73.1%) | 91.7% (90.4%-92.9%) | 0.717 (0.670-0.756) |
| Passing | 548 (26.2%) | 92.6% (90.5%-94.2%) | 86.5% (82.5%-89.7%) | 93.1% (91.0%-94.7%) | 85.6% (81.6%-88.7%) | 90.5% (87.8%-92.7%) | 0.788 (0.728-0.837) |
| Poor to Failing | 130 (5.5%) | 85.3% (79.1%-89.9%) | 81.8% (73.3%-88.1%) | 86.5% (80.1%-91.2%) | 80.4% (72.0%-86.5%) | 83.8% (76.6%-89.2%) | 0.670 (0.522-0.779) |

(Conclusion)

As observed from the above examples, an objective assessment of UC, that is, a combination of endoscopic and histological assessments, is considered to be important for selecting treatment methods for UC and for monitoring the response to pharmacotherapy. In particular, the assessment is considered to be important for the design and assessment of appropriate clinical trials. Unfortunately, however, assessments by specialist can be inconsistent and are likely to be influenced by the individual experience of the specialist. Therefore, clinical trials require independent assessment by a neutral third party.

In view of these, the inventors of the technique according to the present disclosure have constructed a DNUC for assessing mucosal inflammation and prediction of histological inflammation based on endoscopic images of UC. Since the diagnostic ability of the constructed DNUC is considered to be comparable to the ability of an experienced specialist, the DNUC is considered to be usable for objective assessment of endoscopic images.

Specifically, DNUC indicated higher accuracy and higher consistency in assessment of endoscopic remission compared to endoscopists. In addition, in the UCEIS scoring, the ICC between DNUC and endoscopists was 0.861. Consequently, DNUC is considered to be clinically competent.

AI systems such as DNUC take a short screening time and a little labor, making it possible to obtain the results immediately after endoscopy. As indicated by the results of the above examples, DNUC can obviously implement objective and consistent endoscopic assessment in real time. According to this result, DNUC can solve problems such as assessment discrepancies that occur among a plurality of endoscopists. Therefore, DNUC is expected to be effectively utilized in both clinical practice and clinical trials.

Furthermore, referring to studies on UC, patients who have achieved clinical and endoscopic remissions might still have histologically active disease and thus are at high risk of recurrence. That is, since the agreement between the endoscopic index and the histological index is gradual, it is considered important to repeat the biopsy in order to judge the remission by the histological index.

Typically, biopsy for histological assessment is performed by collecting colonic mucosa during colonoscopy, and thus, the assessment is made for a limited region. By contrast, DNUC can be assessed in any region of the colonic mucosa. In particular, the present example has demonstrated that DNUC can predict histological remission with high accuracy and high consistency. According to this, DNUC can assess histological remission without using biopsy specimens, and therefore DNUC is also expected to contribute to reduction of medical expenses.

As described above, the DNUC constructed in the present example can assess mucosal inflammation in UC patients with the same accuracy as an endoscopist. In addition, the DNUC constructed in the present example can predict histological remission without using a mucosal specimen. It can be seen that the DNUC constructed in the present example is an objective and consistent assessment method that is applicable in both clinical practice and clinical trials.

5. Hardware Configuration Example

Figure 10:
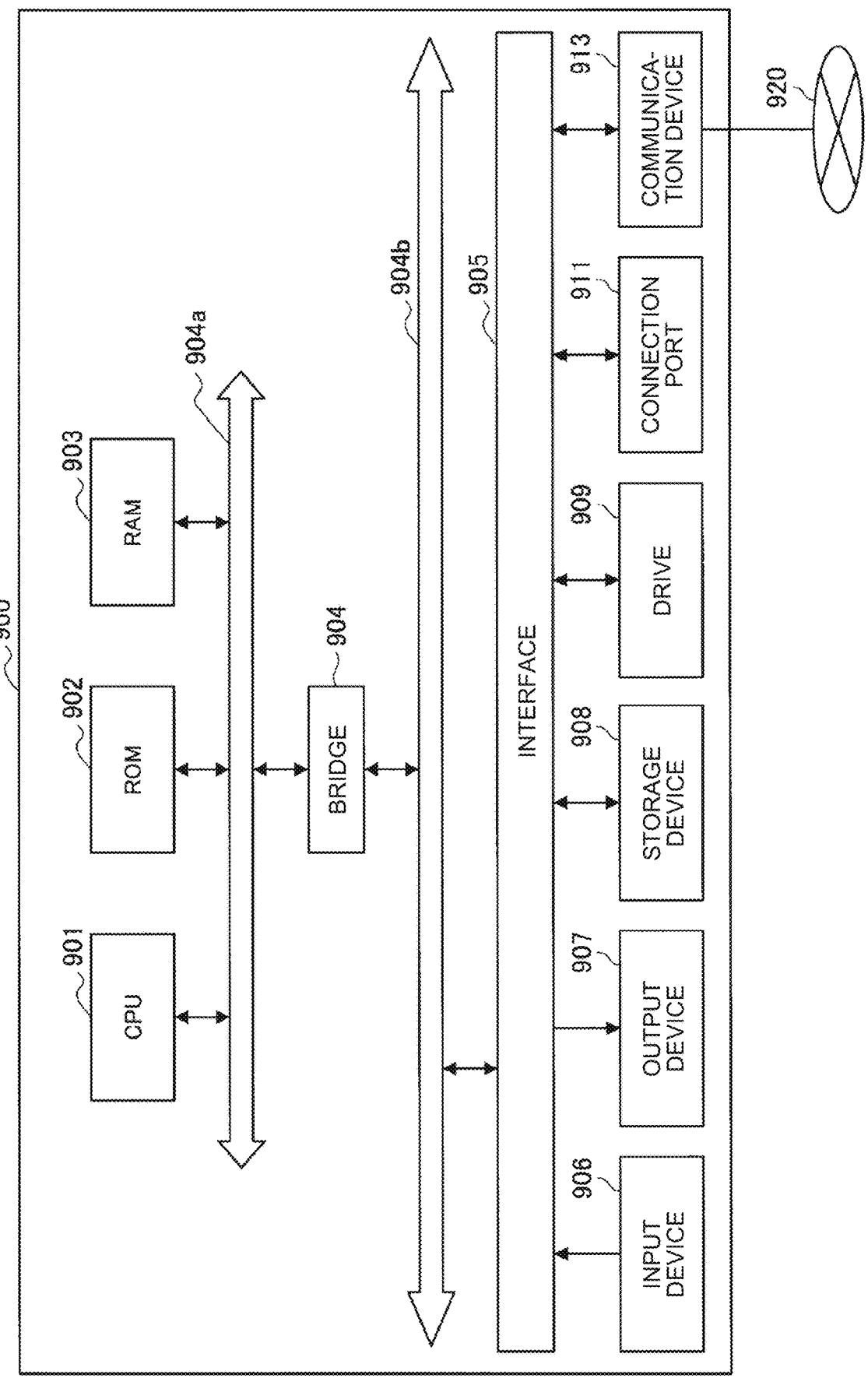
FIG. 10 is a diagram illustrating a hardware configuration example of the medical support system according to the same embodiment.

An example of a hardware configuration such as the derivation device included in the medical support system 1000 according to the present embodiment will be described with reference to FIG. 10. FIG. 10 is a block diagram illustrating an example of a hardware configuration such as the derivation device according to the present embodiment.

As illustrated in FIG. 10, an information processing device 900 includes a central processing unit (CPU) 901, a read only memory (ROM) 902, a random access memory (RAM) 903, and a host bus 904a. Further, the information processing device 900 includes a bridge 904, an external bus 904b, an interface 905, an input device 906, an output device 907, a storage device 908, a drive 909, a connection port 911, and a communication device 913. The information processing device 900 may have a processing circuit such as an electric circuit, a DSP, or an ASIC in place of or in combination with the CPU 901.

The CPU 901 functions as an arithmetic processing device or a control device, and controls the overall operation in the information processing device 900 according to various programs. The CPU 901 may be a microprocessor. The ROM 902 stores programs and calculation parameters used by the CPU 901. The RAM 903 temporarily stores a program used in the execution of the CPU 901, parameters that change appropriately in the execution, or the like. The CPU 901 can function as the assessment derivation unit 124 illustrated in FIG. 3, for example.

The CPU 901, ROM 902, and RAM 903 are connected to each other by the host bus 904a including a CPU bus or the like. The host bus 904a is connected to the external bus 904b such as a Peripheral Component Interconnect/Interface (PCI) bus via the bridge 904. There is no need to separate the host bus 904a, the bridge 904, and the external bus 904b from each other, and these functions may be implemented on one bus.

The input device 906 is actualized by a device to which the user input information, such as a mouse, a keyboard, a touch panel, a button, a microphone, a switch, or a lever. Furthermore, the input device 906 may be, for example, a remote control device using infrared rays or other radio waves, or an externally connected device such as a mobile phone or a PDA that supports the operation of the information processing device 900. Furthermore, the input device 906 may include, for example, an input control circuit that generates an input signal based on the information input by the user using the above input means and outputs the input signal to the CPU 901. By operating the input device 906, the user of the information processing device 900 can input various data to the information processing device 900 and instruct the processing operation.

The output device 907 is formed by a device capable of visually or audibly notifying the user of acquired information. Examples of such devices include display devices such as CRT display devices, liquid crystal display devices, plasma display devices, EL display devices, laser projectors, LED projectors, and lamps, and audio output devices such as speakers and headphones. The output device 907 outputs the results obtained by various processes performed by the information processing device 900, for example. Specifically, the output device 907 may visually display the results obtained by various processes performed by the information processing device 900 in various formats such as texts, images, tables, and graphs. Alternatively, the output device 907 may convert an audio signal composed of reproduced audio data, acoustic data, or the like into an analog signal and output the signal audibly. The output device 907 can function as the display device 130 illustrated in FIG. 3, for example.

The storage device 908 is a data storage device formed as an example of a storage unit of the information processing device 900. The storage device 908 is actualized by, for example, a magnetic storage device such as an HDD, a semiconductor storage device, an optical storage device, an optical magnetic storage device, or the like. The storage device 908 may include a storage medium, a recording device that records data on the storage medium, a reading device that reads data from the storage medium, a deleting device that deletes the data recorded on the storage medium, and the like. The storage device 908 stores programs executed by the CPU 901, various data, as well as various data acquired from the outside, and the like. The storage device 908 stores, for example, an affected site image or an assessment image used in the assessment derivation unit 124 illustrated in FIG. 3, various parameters used when deriving a tile assessment value, or the like.

The drive 909 is a reader/writer for a storage medium, and is built in or externally connected to the information processing device 900. The drive 909 reads information recorded on a removable storage medium such as a mounted magnetic disk, optical disk, magneto-optical disk, or semiconductor memory, and outputs the read information to the RAM 903. The drive 909 can also write information to the removable storage medium.

The connection port 911 is an interface connected to an external device. For example, the connection port 911 may be a connection port with an external device, capable of transmitting data by a Universal Serial Bus (USB) or the like.

Figure 3:
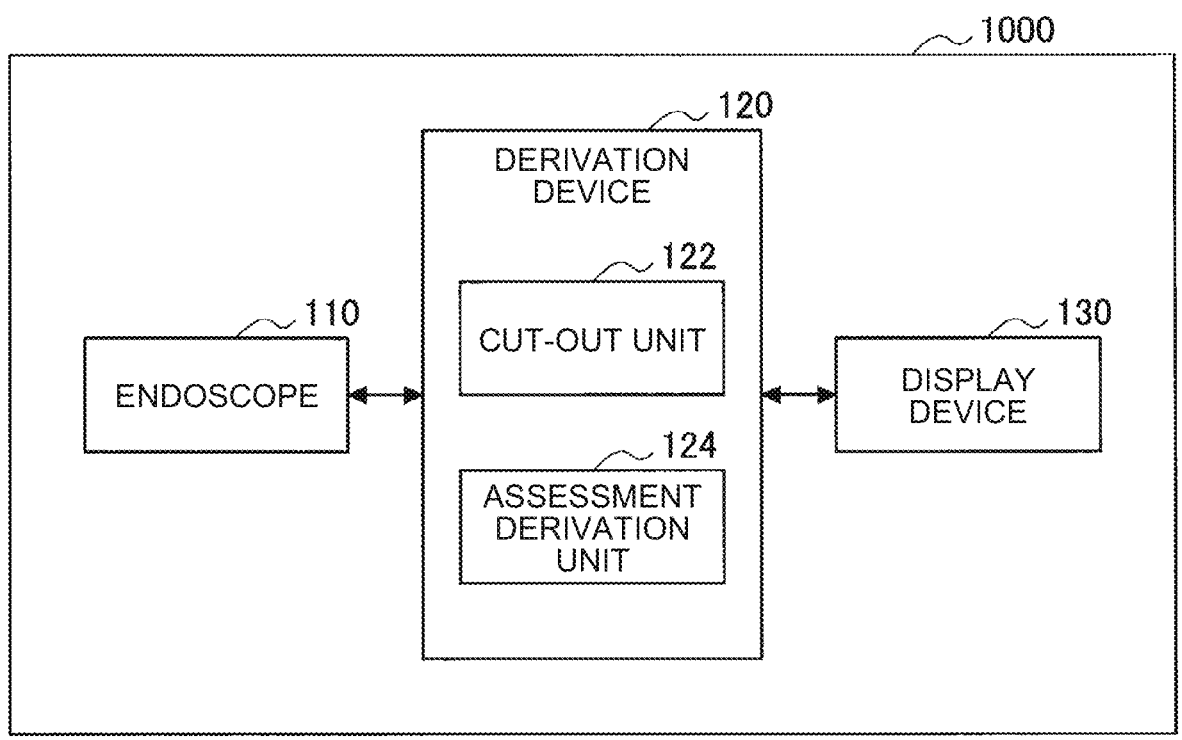
FIG. 3 is a block diagram illustrating an example of a configuration of the medical support system according to the same embodiment.

The communication device 913 is, for example, a communication interface formed by a communication device or the like for connecting to a network 920. The communication device 913 may be, for example, a communication card for wired or wireless Local Area Network (LAN), Long Term Evolution (LTE), Bluetooth (registered trademark), Wireless USB (WUSB), or the like. Further, the communication device 913 may be a router for optical communication, an Asymmetric Digital Subscriber Line (ADSL) router, a modem for various communications, or the like. The communication device 913 can transmit and receive signals or the like to and from the Internet and other communication devices in accordance with a predetermined protocol such as TCP/IP. With the communication device 913, for example, as illustrated in FIG. 3, input and output of various types of information can be performed among the derivation device 120, the endoscope 110, and the display device 130.

The network 920 is a wired or wireless transmission path for information transmitted from a device connected to the network 920. For example, the network 920 may include a public network such as the Internet, a telephone network, and a satellite communication network, or various local area networks (LANs) including Ethernet (registered trademark), wide area networks (WANs), or the like. Furthermore, the network 920 may include a dedicated network such as an Internet protocol-virtual private network (IP-VPN).

In addition, it is also possible to create a computer program for implementing the same functions as individual configurations of the medical support system 1000 according to the present embodiment described above when the program is loaded to hardware such as a CPU, ROM, and RAM built in the information processing device 900. Furthermore, a recording medium in which the computer program is stored can also be included in the scope of the technique according to the present disclosure.

The preferred embodiments of the present disclosure have been described in detail above with reference to the accompanying drawings. However, the technical scope of the present disclosure is not limited to such examples. It will be apparent to those skilled in the art of the present disclosure that various modifications and alterations can be conceived within the scope of the technical idea described in the claims and naturally fall within the technical scope of the present disclosure.

Furthermore, the effects described in the present specification are merely illustrative or exemplary and are not limited. That is, the technique according to the present disclosure can exhibit other effects that are apparent to those skilled in the art from the description of the present specification in addition to or instead of the above effects.

Note that the following configurations also belong to the technical scope of the present disclosure.

(1)
A medical support system comprising:
a derivation device that derives an assessment value for an affected site based on an affected site image obtained by imaging the affected site; and
a display device that presents the assessment value to a user,
wherein the derivation device includes: a cut-out unit that cuts out the affected site image as a plurality of tile images having tile shapes; and an assessment derivation unit that derives a tile assessment value representing an assessment of the affected site in the plurality of the tile images by using a determiner obtained by machine learning.

(2)
The medical support system according to (1), wherein the assessment derivation unit further estimates an overall assessment value regarding a whole of the affected site image based on the tile assessment value.

(3)
The medical support system according to (2), wherein the cut-out unit cuts out the affected site image as the plurality of the tile images having a size capable of determining a pathological condition of the affected site.

(4)
The medical support system according to (2) or (3), wherein the assessment derivation unit selects the tile image to be used for estimating the overall assessment value from the plurality of the tile images in accordance with luminance of the plurality of the tile images.

(5)
The medical support system according to (4), wherein the assessment derivation unit uses, in estimating the overall assessment value, the tile image having the luminance being a first threshold or more and being a second threshold or less, the second threshold being greater than the first threshold.

(6)
The medical support system according to any one of (2) to (5), wherein the display device displays the plurality of the tile images indicating different display modes in accordance with the tile assessment value so as to be superimposed over the affected site image.

(7)
The medical support system according to (6), wherein the derivation device further derives reliability of the tile assessment value.

(8)
The medical support system according to (7), wherein the display device further displays the plurality of the tile images indicating different display modes in accordance with the reliability so as to be superimposed over the affected site image.

(9)
The medical support system according to any one of (2) to (8), wherein the assessment derivation unit estimates the overall assessment value by using at least any one or more of a mean value, a maximum value, or probability distribution of the assessment values in the tile assessment values.

(10)
The medical support system according to (6) or (8),
wherein the affected site image is captured by an endoscope, and
the display device displays a position of the endoscope within a body of a patient, and displays the overall assessment value corresponding to the position within the body of the patient.

(11)
The medical support system according to (6) or (8), wherein a part of the affected site image is displayed as an enlarged image on the display device in accordance with the tile assessment value.

(12)
The medical support system according to any one of (3) to (11), wherein the cut-out unit cuts out the affected site image as the tile image having a polygonal shape, and the cut-out unit cuts out the affected site image so that the polygonal shape has a circumscribed circle being 5 mm or more and 15 mm or less.

(13)
The medical support system according to (6) or (8), wherein the tile assessment value is a tile assessment value related to at least any one or more of assessments for items of bleeding, tumor, or visible vascular pattern of the affected site, or assessments for pathological examination items.

(14)
The medical support system according to (13), wherein the display device displays the affected site image, and the affected site image displayed in the superimposed manner for each of the items, so as to be arranged side by side.

(15)

A medical support device comprising:
a cut-out unit that cuts out an affected site image obtained by imaging an affected site as a plurality of tile images having tile shapes;
an assessment derivation unit that derives a tile assessment value representing an assessment of the affected site in the plurality of the tile images by using a determiner obtained by machine learning; and
a display control unit that controls a display device that presents the tile assessment value to a user.

(16)

A medical support method comprising:
cutting out, by a derivation device, an affected site image obtained by imaging an affected site as a plurality of tile images having tile shapes, and deriving, by the derivation device, a tile assessment value representing an assessment of the affected site in the plurality of the tile images by using a determiner obtained by machine learning; and
presenting, by a display device, the tile assessment value to a user.

REFERENCE SIGNS LIST

110 ENDOSCOPE
120 DERIVATION DEVICE
122 CUT-OUT UNIT
124 ASSESSMENT DERIVATION UNIT
130 DISPLAY DEVICE

The invention claimed is:

1. A medical support system comprising:
assessment circuitry configured to:
cut out an affected site image obtained by imaging an affected site as a plurality of tile images having tile shapes; and determine a tile assessment value representing an assessment of the affected site in the plurality of the tile images based on a learned model by machine learning.

2. The medical support system according to claim 1, wherein the assessment circuitry is further configured to estimate an overall assessment value regarding a whole of the affected site image based on the tile assessment value.

3. The medical support system according to claim 2, wherein the assessment circuitry is configured to cut out the affected site image as the plurality of the tile images having a size capable of determining a pathological condition of the affected site.

4. The medical support system according to claim 2, wherein the assessment circuitry is configured to select the tile image to be used for estimating the overall assessment value from the plurality of the tile images in accordance with luminance of the plurality of the tile images.

5. The medical support system according to claim 4, wherein the assessment circuitry is configured to use, in estimating the overall assessment value, the tile image having the luminance of a first threshold or more and of a second threshold or less, the second threshold being greater than the first threshold.

6. The medical support system according to claim 2, further including a display device, wherein the assessment circuitry is configured to control the display device to display the plurality of the tile images indicating different display modes in accordance with the tile assessment value, superimposed over the affected site image.

7. The medical support system according to claim 6, wherein the assessmet circuitry is configured to derive a reliability of the tile assessment value.

8. The medical support system according to claim 7, wherein the assessment circuitry is configured to control the display device to display the plurality of the tile images indicating different display modes in accordance with the reliability, superimposed over the affected site image.

9. The medical support system according to claim 2, wherein the assessment circuitry is configured to estimate the overall assessment value by using at least any one or more of a mean value, a maximum value, or a probability distribution of the assessment values in the tile assessment values.

10. The medical support system according to claim 6, wherein the affected site image is captured by an endoscope, and
the assessment circuitry is configured to control the display device to display a position of the endoscope within a body of a patient, and to display the overall assessment value corresponding to the position within the body of the patient.

11. The medical support system according to claim 6, wherein a part of the affected site image is displayed as an enlarged image on the display device in accordance with the tile assessment value.

12. The medical support system according to claim 3, wherein the assessment circuitry is configured to cut out the affected site image as the tile image having a polygonal shape, and to cut out the affected site image so that the polygonal shape has a circumscribed circle of 5 mm or more and 15 mm or less.

13. The medical support system according to claim 6, wherein the tile assessment value is a tile assessment value related to at least any one or more of assessments for items of bleeding, tumor, or visible vascular pattern of the affected site, or assessments for pathological examination items.

14. The medical support system according to claim 13, wherein the assessment circuitry is configured to control the display device to display the affected site image and the affected site image displayed in the superimposed manner for each of the items, arranged side by side.

15. A medical support device comprising:
assessment circuitry configured to:
cut out an affected site image obtained by imaging an affected site as a plurality of tile images having tile shapes; and
determine a tile assessment value representing an assessment of the affected site in the plurality of the tile images based on a learned model by machine learning.

16. A medical support method executed by assessment circuitry, the method comprising:
cutting out an affected site image obtained by imaging an affected site as a plurality of tile images having tile shapes; and determining a tile assessment value representing an assessment of the affected site in the plurality of the tile images based on a learned model by machine learning.

17. The medical support system according to claim 1, wherein the assessment circuitry is further configured to control a display device to present the tile assessment value to a user.

18. The medical support device according to claim 15, wherein the assessment circuitry is further configured to control a display device to present the tile assessment value to a user.

19. The medical support method according to claim 16, further comprising controlling a display device to present the tile assessment value to a user.

\* \* \* \* \*